US010292756B2

(12) United States Patent
Shikhman et al.

(10) Patent No.: US 10,292,756 B2
(45) Date of Patent: *May 21, 2019

(54) SYSTEMS AND METHODS FOR TREATING TISSUE WITH RADIOFREQUENCY ENERGY

(71) Applicant: Mederi RF, LLC, Houston, TX (US)

(72) Inventors: Oleg Shikhman, Trumbull, CT (US); Ronald L. Green, Bethel, CT (US); Jeffrey Radziunas, Wallingford, CT (US)

(73) Assignee: Mederi RF, LLC, Houston, TX (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/607,301

(22) Filed: May 26, 2017

(65) Prior Publication Data

US 2017/0265928 A1  Sep. 21, 2017

Related U.S. Application Data

(60) Division of application No. 14/708,209, filed on May 9, 2015, now Pat. No. 9,675,404, which is a
(Continued)

(51) Int. Cl.
*A61B 18/14* (2006.01)
*A61B 18/18* (2006.01)
(Continued)

(52) U.S. Cl.
CPC .......... *A61B 18/14* (2013.01); *A61B 18/1206* (2013.01); *A61B 18/18* (2013.01);
(Continued)

(58) Field of Classification Search
CPC ......... A61B 18/02; A61B 18/08; A61B 18/12; A61B 18/1206; A61B 18/14;
(Continued)

(56) References Cited

U.S. PATENT DOCUMENTS 1,798,902 A  3/1931 Raney
3,517,128 A  6/1970 Hines
(Continued)

FOREIGN PATENT DOCUMENTS

CN  1871609  11/2006
DE  4303882  2/1995
(Continued)

OTHER PUBLICATIONS

Castell, D.O. Gastroesophageal Reflux Disease: Current Strategies for Patient Management: Arch Fam. Med 5(4): 221-7. Apr. 5, 1996.
(Continued)

*Primary Examiner* — Michael F Peffley
*Assistant Examiner* — Khadijeh A Vahdat
(74) *Attorney, Agent, or Firm* — Neil D. Gershon

(57) ABSTRACT

A system for controlling operation of a radiofrequency treatment device to apply radiofrequency energy to tissue to treat tissue to create lesions without ablating the tissue. The system includes a device having flexible outer tube, an expandable basket having a plurality of arms movable from a collapsed position to an expanded position, a plurality of electrodes movable from a retracted position to an extended position to extend through the openings in the arms, and an advancer slidably disposed within the outer tube to move the electrodes. An elongated spacer is positioned within the outer tube, the spacer having a central lumen to receive the advancer and to maintain a central position of the advancer.

20 Claims, 27 Drawing Sheets

Related U.S. Application Data continuation-in-part of application No. 13/867,042, filed on Apr. 20, 2013, now Pat. No. 9,474,565, which is a continuation-in-part of application No. 12/924,155, filed on Sep. 22, 2010, now abandoned.

(60) Provisional application No. 62/009,222, filed on Jun. 7, 2014, provisional application No. 61/664,960, filed on Jun. 27, 2012, provisional application No. 61/277,260, filed on Sep. 22, 2009.

(51) Int. Cl.
*A61B 18/12* (2006.01)
*G06F 3/0481* (2013.01)
*A61B 34/00* (2016.01)
*A61B 18/08* (2006.01)
*A61B 18/00* (2006.01)
*A61B 18/02* (2006.01)
*A61B 18/04* (2006.01)
*A61N 7/02* (2006.01)

(52) U.S. Cl.
CPC ............ *A61B 34/25* (2016.02); *G06F 3/0481* (2013.01); *A61B 18/02* (2013.01); *A61B 18/08* (2013.01); *A61B 18/1477* (2013.01); *A61B 18/1485* (2013.01); *A61B 18/1492* (2013.01); *A61B 18/1815* (2013.01); *A61B 2018/005* (2013.01); *A61B 2018/00029* (2013.01); *A61B 2018/00267* (2013.01); *A61B 2018/00482* (2013.01); *A61B 2018/00488* (2013.01); *A61B 2018/00494* (2013.01); *A61B 2018/00553* (2013.01); *A61B 2018/00577* (2013.01); *A61B 2018/00642* (2013.01); *A61B 2018/00678* (2013.01); *A61B 2018/00702* (2013.01); *A61B 2018/00708* (2013.01); *A61B 2018/00761* (2013.01); *A61B 2018/00791* (2013.01); *A61B 2018/00916* (2013.01); *A61B 2018/0212* (2013.01); *A61B 2018/044* (2013.01); *A61B 2018/143* (2013.01); *A61B 2018/1425* (2013.01); *A61B 2018/1467* (2013.01); *A61B 2018/1475* (2013.01); *A61B 2018/1861* (2013.01); *A61B 2034/252* (2016.02); *A61B 2034/254* (2016.02); *A61B 2218/002* (2013.01); *A61B 2218/007* (2013.01); *A61N 7/022* (2013.01)

(58) Field of Classification Search
CPC ............ A61B 18/1477; A61B 18/1485; A61B 18/1492; A61B 18/18; A61B 18/1815; A61B 2018/00029; A61B 2018/00267; A61B 2018/00482; A61B 2018/00488; A61B 2018/00494; A61B 2018/005; A61B 2018/00553; A61B 2018/00577; A61B 2018/00642; A61B 2018/00678; A61B 2018/00702; A61B 2018/00708; A61B 2018/00761; A61B 2018/00791; A61B 2018/00916; A61B 2018/0212; A61B 2018/044; A61B 2018/1425; A61B 2018/143; A61B 2018/1467; A61B 2018/1475; A61B 2018/1861; A61B 2034/252; A61B 2034/254; A61B 2218/002; A61B 2218/007; A61B 34/25; A61N 7/022; G06F 3/0481
USPC .................................................... 606/20–50
See application file for complete search history.

(56) References Cited

U.S. PATENT DOCUMENTS

| | | |
|---|---|---|
| 3,901,241 A | 8/1975 | Allen, Jr. |
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |
| 4,858,615 A | 8/1989 | Meinema |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 4,998,933 A | 3/1991 | Eggers et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,114,423 A | 5/1992 | Kasprzyk et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,233,515 A | 8/1993 | Cosman |
| 5,236,413 A | 8/1993 | Feiring |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,305,696 A | 4/1994 | Mendenhall |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,330,518 A | 7/1994 | Neilson et al. |
| 5,334,193 A | 8/1994 | Nardella |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,347 A | 11/1994 | Nguyen |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |

(56) References Cited

U.S. PATENT DOCUMENTS

| | | |
|---|---|---|
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,874 A | 1/1995 | Jackson et al. |
| 5,383,876 A | 1/1995 | Nardella |
| 5,383,917 A | 1/1995 | Desai et al. |
| 5,385,544 A | 1/1995 | Edwards et al. |
| 5,385,917 A | 1/1995 | Ueno et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,415,657 A | 5/1995 | Taymor-Luria |
| 5,421,819 A | 6/1995 | Edwards et al. |
| 5,423,808 A | 6/1995 | Edwards et al. |
| 5,423,811 A | 6/1995 | Ellman et al. |
| 5,423,812 A | 6/1995 | Ellman et al. |
| 5,433,198 A | 7/1995 | Desai |
| 5,433,739 A | 7/1995 | Sluijter et al. |
| 5,435,805 A | 7/1995 | Edwards |
| 5,441,499 A | 8/1995 | Fritzsch |
| 5,443,463 A | 8/1995 | Stern et al. |
| 5,443,470 A | 8/1995 | Stern et al. |
| 5,454,782 A | 10/1995 | Perkins |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,609,151 A | 3/1997 | Mulier et al. |
| 5,624,439 A | 4/1997 | Edwards et al. |
| 5,651,780 A | 7/1997 | Jackson et al. |
| 5,672,153 A | 9/1997 | Lax et al. |
| 5,672,174 A | 9/1997 | Gough et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,733,319 A | 3/1998 | Neilson et al. |
| 5,738,096 A | 4/1998 | Ben-Haim |
| 5,742,718 A | 4/1998 | Harman et al. |
| 5,743,903 A | 4/1998 | Stern et al. |
| 5,769,847 A | 6/1998 | Panescu et al. |
| 5,800,482 A | 9/1998 | Pomeranz et al. |
| 5,827,276 A | 10/1998 | Le Veen et al. |
| 5,830,213 A | 11/1998 | Panescu et al. |
| 5,836,874 A | 11/1998 | Swanson et al. |
| 5,843,076 A | 12/1998 | Webster, Jr. et al. |
| 5,848,969 A | 12/1998 | Panescu et al. |
| 5,855,576 A | 1/1999 | Le Veen et al. |
| 5,860,974 A | 1/1999 | Abele |
| 5,871,469 A | 2/1999 | Eggers et al. |
| 5,871,481 A | 2/1999 | Kannenberg et al. |
| 5,871,483 A | 2/1999 | Jackson et al. |
| 5,876,336 A | 3/1999 | Swanson et al. |
| 5,891,030 A | 4/1999 | Johnson et al. |
| 5,916,163 A | 6/1999 | Panescu et al. |
| 5,931,835 A | 8/1999 | Mackey |
| 5,957,920 A | 9/1999 | Baker |
| 5,957,961 A | 9/1999 | Maguire et al. |
| 6,004,269 A | 12/1999 | Crowley et al. |
| 6,006,755 A | 12/1999 | Edwards |
| 6,009,877 A | 1/2000 | Edwards |
| 6,014,581 A | 1/2000 | Whayne et al. |
| 6,023,638 A | 2/2000 | Swanson |
| 6,044,846 A | 4/2000 | Edwards |
| 6,056,744 A | 5/2000 | Edwards |
| 6,063,082 A | 5/2000 | DeVore et al. |
| 6,073,052 A | 6/2000 | Zelickson et al. |
| 6,092,528 A | 7/2000 | Edwards |
| 6,106,460 A | 8/2000 | Panescu et al. |
| 6,165,169 A | 12/2000 | Panescu et al. |
| 6,197,022 B1 | 3/2001 | Baker |
| 6,231,569 B1 | 5/2001 | Bek et al. |
| 6,235,022 B1 | 5/2001 | Hallock et al. |
| 6,241,725 B1 | 6/2001 | Cosman |
| 6,254,598 B1 | 7/2001 | Edwards et al. |
| 6,266,551 B1 | 7/2001 | Osadchy et al. |
| 6,273,886 B1 | 8/2001 | Edwards et al. |
| 6,355,031 B1 | 3/2002 | Edwards et al. |
| 6,358,245 B1 | 3/2002 | Edwards et al. |
| 6,387,092 B1 | 5/2002 | Burnside et al. |
| 6,389,311 B1 | 5/2002 | Whayne et al. |
| 6,391,024 B1 | 5/2002 | Sun et al. |
| 6,402,744 B2 | 6/2002 | Edwards et al. |
| 6,405,732 B1 | 6/2002 | Edwards et al. |
| 6,440,128 B1 | 8/2002 | Edwards et al. |
| 6,464,689 B1 | 10/2002 | Qin et al. |
| 6,464,697 B1 | 10/2002 | Edwards et al. |
| 6,478,793 B1 | 11/2002 | Cosman et al. |
| 6,544,226 B1 | 4/2003 | Gaiser et al. |
| 6,547,776 B1 | 4/2003 | Gaiser et al. |
| 6,575,969 B1 | 6/2003 | Rittman et al. |
| 6,589,238 B2 | 7/2003 | Edwards et al. |
| 6,613,047 B2 | 9/2003 | Edwards |
| 6,645,201 B1 | 11/2003 | Utley et al. |
| 6,647,298 B2 | 11/2003 | Abrahamson et al. |
| 6,695,806 B2 | 2/2004 | Gelfand et al. |
| 6,699,243 B2 | 3/2004 | West et al. |
| 6,733,495 B1 | 5/2004 | Bek et al. |
| 6,740,082 B2 | 5/2004 | Shadduck |
| 6,783,523 B2 | 8/2004 | Qin et al. |
| 6,790,207 B2 | 9/2004 | Utley et al. |
| 6,802,841 B2 | 10/2004 | Utley et al. |
| 6,827,713 B2 | 12/2004 | Bek et al. |
| 6,835,202 B2 | 12/2004 | Harth et al. |
| 7,258,688 B1 | 8/2007 | Baylis et al. |
| 7,731,684 B2 | 6/2010 | Gaiser et al. |
| 8,235,979 B2 | 8/2012 | Morgan et al. |
| 8,282,631 B2 | 10/2012 | Davalos et al. |
| 8,454,595 B2 | 6/2013 | Edwards et al. |
| 8,647,298 B2 | 2/2014 | West et al. |
| 8,728,074 B2 | 5/2014 | West et al. |
| 8,894,646 B2 | 11/2014 | Edwards et al. |
| 2001/0034518 A1 | 10/2001 | Edwards |
| 2002/0151871 A1 | 10/2002 | Gaiser et al. |
| 2002/0162555 A1 | 11/2002 | West et al. |

(56) References Cited

U.S. PATENT DOCUMENTS

| | | |
|---|---|---|
| 2002/0193787 A1 | 12/2002 | Qin et al. |
| 2002/0198519 A1 | 12/2002 | Qin et al. |
| 2003/0078490 A1 | 4/2003 | Damasco et al. |
| 2003/0109778 A1 | 6/2003 | Rashidi |
| 2004/0089313 A1 | 5/2004 | Utley et al. |
| 2004/0133189 A1 | 7/2004 | Sakurai |
| 2005/0107667 A1 | 5/2005 | Danitz et al. |
| 2005/0143632 A1 | 6/2005 | Elaz et al. |
| 2005/0154386 A1 | 7/2005 | West |
| 2005/0187546 A1 | 8/2005 | Bek et al. |
| 2006/0046031 A1 | 3/2006 | Janevski |
| 2007/0219551 A1 | 9/2007 | Honour et al. |
| 2008/0097422 A1 | 4/2008 | Edwards et al. |
| 2008/0147059 A1 | 6/2008 | Bee |
| 2008/0154253 A1 | 6/2008 | Damasco et al. |
| 2009/0171184 A1 | 7/2009 | Farberov et al. |
| 2010/0130836 A1 | 5/2010 | Malchano et al. |
| 2010/0204694 A1 | 8/2010 | Mehta et al. |
| 2011/0257646 A1 | 10/2011 | Utley et al. |
| 2013/0237979 A1 | 9/2013 | Shikhman et al. |
| 2014/0135686 A1 | 5/2014 | Jimenez et al. |

FOREIGN PATENT DOCUMENTS

| | | |
|---|---|---|
| DE | 3838840 | 2/1997 |
| EP | 0139607 | 5/1985 |
| EP | 0608609 | 8/1994 |
| EP | 0765813 | 4/1997 |
| JP | 2004-105502 | 4/2004 |
| WO | WO-91/01773 | 2/1991 |
| WO | WO-92/10142 | 6/1992 |
| WO | WO-93/08755 | 5/1993 |
| WO | WO-94/10925 | 5/1994 |
| WO | WO-94/21165 | 9/1994 |
| WO | WO-94/21178 | 9/1994 |
| WO | WO-94/22366 | 10/1994 |
| WO | WO-94/26178 | 11/1994 |
| WO | WO-95/18575 | 7/1995 |
| WO | WO-95/19142 | 7/1995 |
| WO | WO-95/25472 | 9/1995 |
| WO | WO-96/00042 | 1/1996 |
| WO | WO-96/16606 | 1/1996 |
| WO | WO-96/29946 | 1/1996 |
| WO | WO-96/36860 | 11/1996 |
| WO | WO-96/41654 | 12/1996 |
| WO | WO-97/06857 | 2/1997 |
| WO | WO 97/25011 | 7/1997 |
| WO | WO-97/32532 | 9/1997 |
| WO | WO-97/43971 | 11/1997 |
| WO | WO-99/17671 | 4/1999 |
| WO | WO-00/66052 | 11/2000 |
| WO | WO-01/017452 | 3/2001 |
| WO | WO-01/24721 | 4/2001 |
| WO | WO-04/107989 | 12/2004 |
| WO | WO-08060142 | 5/2008 |
| WO | WO-11/037621 | 3/2011 |

OTHER PUBLICATIONS

Dallemagne, B. et al., "Laparoscopic Nissen Fundoplication: Preliminary," Surgical Laparoscopy & Endoscopy. 1991 1(3): 138-43.

Kelly, KA et al., "Duodenal-gastric reflux and slowed gastric emptying by electrical pacing of the canine duodenal pacesetter potential," Gastroenterology. 1997.72 (3): 429-33.

Reynolds, J.C. "Influence of pathophysiology, severity, and cost on the medical management of gastroesophageal reflux disease," Am J. Health-Syst Pharm. 53 (22 suppl 3): S5-12. Nov. 15, 1996.

Urschel, J.D. "Complications of Antireflux Surgery," Am J. Surg. 1993. 166 (1): 68-70.

Kaneko, et al., Physiological Laryngeal Pacemaker, May 1985, Trans Am Soc. Artif. Intern Organs, vol. XXXI, pp. 293-296.

Mugica, et al. Direct Diaphragm Stimulation, Jan. 1987 PACE, vol. 10, pp. 252-256.

Mugica, et al., Neurostimulation: An Overview, Chapter 21, Preliminary Test of a Muscular Diaphragm Pacing System on Human Patients. 1985. pp. 3. 263-279.

Rice, et al., Endoscopic Paranasal Sinus Surgery, Chapter 5, Endoscopic Paranasal Sinus Surgery, The Technique of Messerklinger, Raven Press, 1988, pp. 75-104.

Rice, et al., Endoscopic Paranasal Sinus Surgery, Chapter 6, Functional Endoscopic Paranasal Sinus Surgery, The Technique of Wigand, Raven Press, 1988, pp. 105-125.

Karlstrom, L.H., et al., Exotopic jejunal pacemakers and enterogastric reflux after Roux gastrectomy; Effect of intestinal pacing. Surgery 1989. 106 (3): 486-495.

Hinder; R.A., et al. "The Technique of Laparoscopic Nissen Fundoplication," Surgical Laparoscopy & Endoscopy. 1992. 2 (3): 265-272.

European Search Report from Application No. PCT/US2015/031660 dated Oct. 28, 2015.

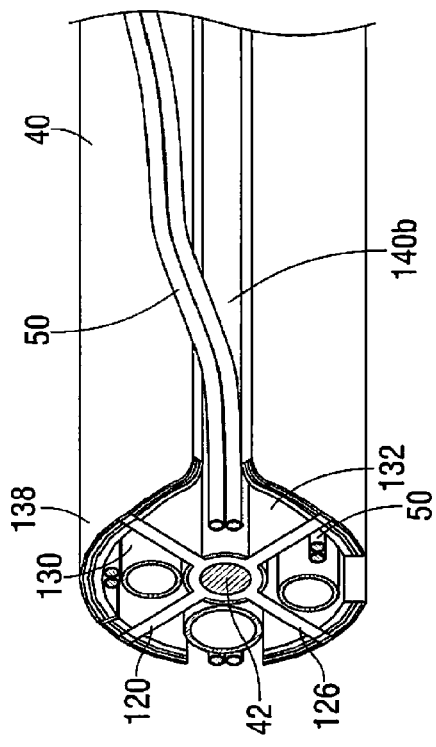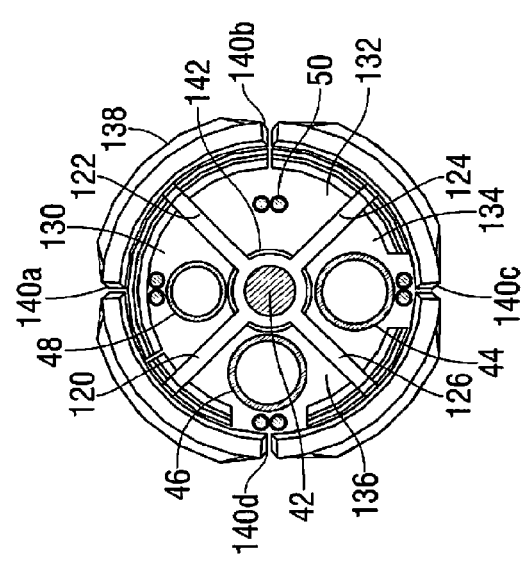

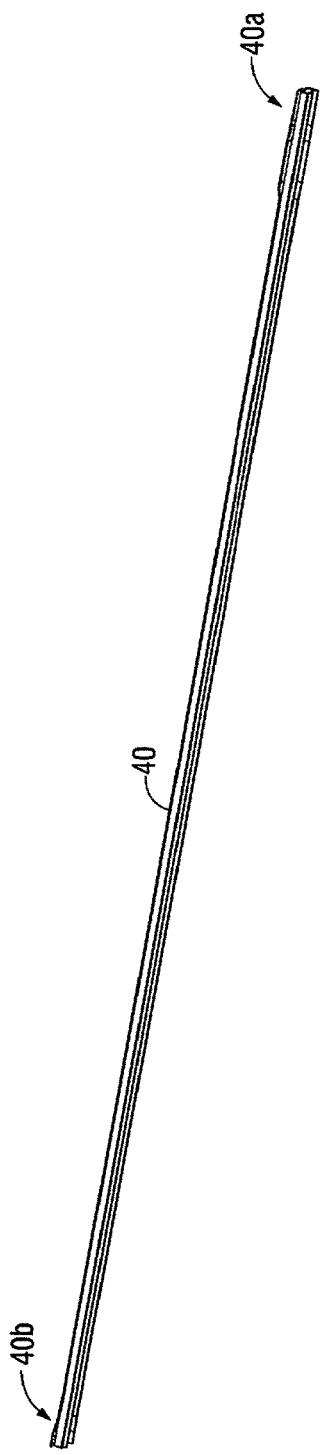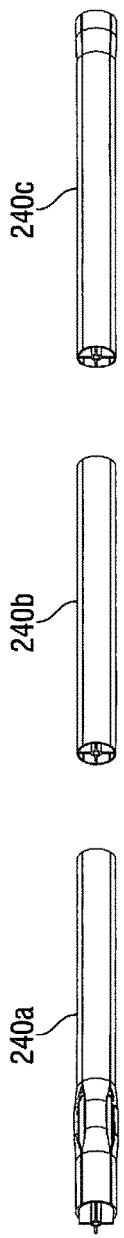
FIG. 10
FIG. 11
FIG. 12

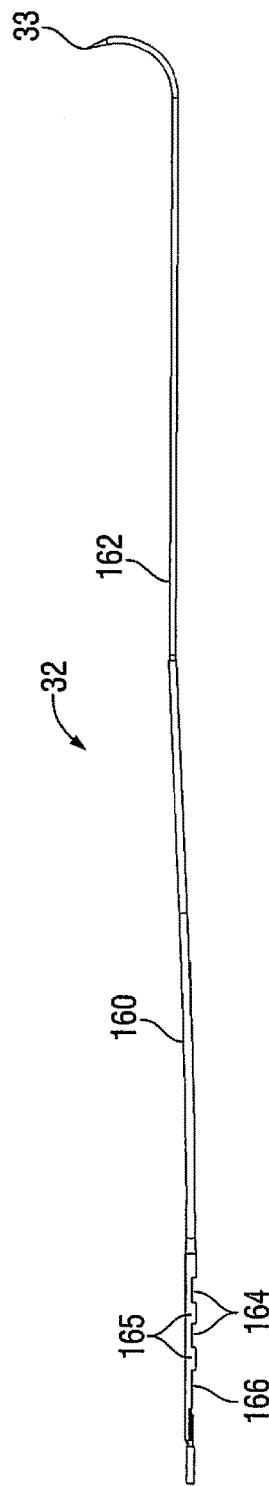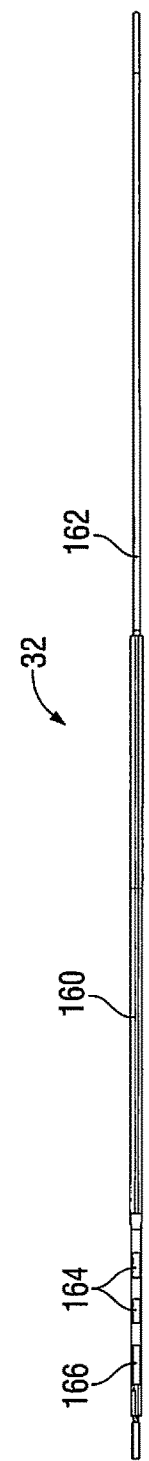
FIG. 19
FIG. 20

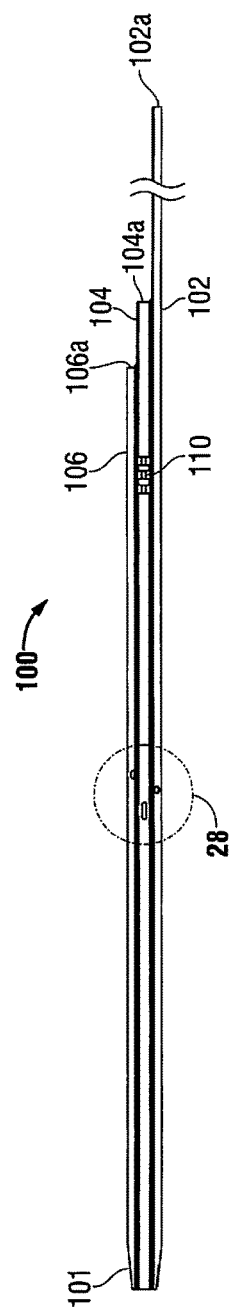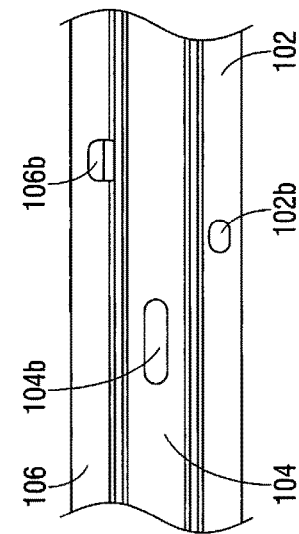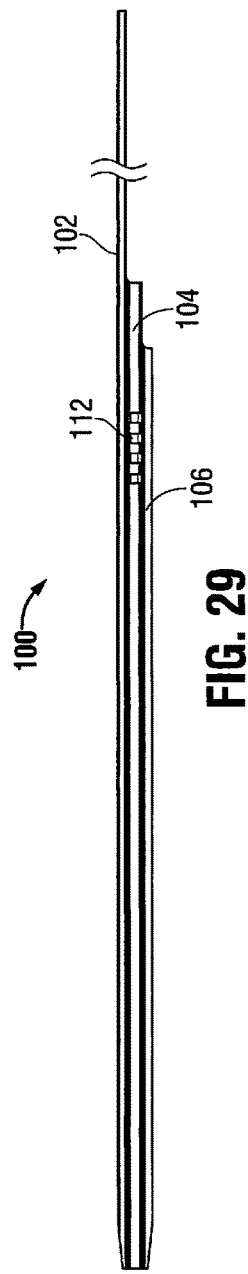

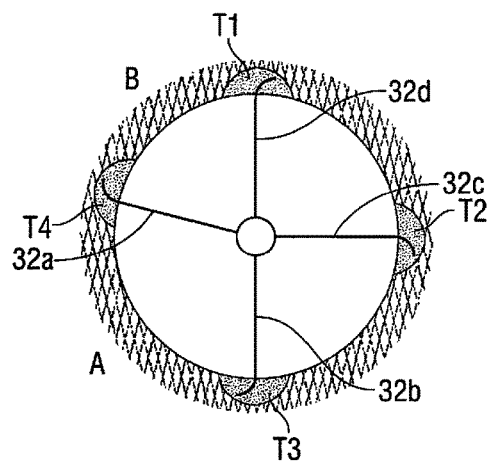
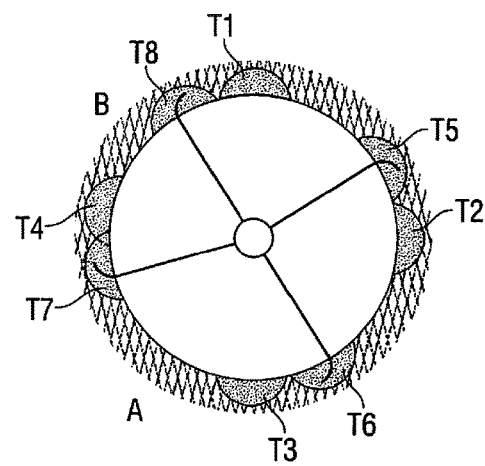
FIG. 35A  FIG. 35B
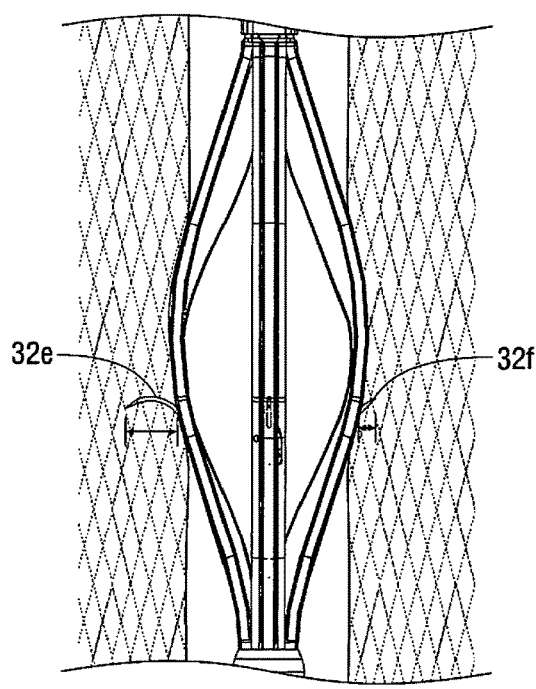
FIG. 35C

SYSTEMS AND METHODS FOR TREATING TISSUE WITH RADIOFREQUENCY ENERGY

RELATED APPLICATIONS

This application is a divisional of application Ser. No. 14/708,209, filed May 9, 2015, now U.S. Pat. No. 9,675,404 which claims the benefit of provisional application Ser. No. 62/009,222 filed Jun. 7, 2014 and is a continuation in part of application Ser. No. 13/867,042, filed Apr. 20, 2013, now U.S. Pat. No. 9,474,565, which claims the benefit of provisional application Ser. No. 61/664,960, filed Jun. 27, 2012 and is a continuation-in-part of application Ser. No. 12/924,155, filed Sep. 22, 2010, now abandoned, which claims the benefit of provisional application Ser. No. 61/277,260 filed Sep. 22, 2009. The entire contents of each of these applications are incorporated herein by reference.

FIELD OF THE INVENTION

In a general sense, the invention is directed to systems and methods for treating interior tissue regions of the body. More specifically, the invention is directed to systems and methods for treating dysfunction in body sphincters and adjoining tissue by applying radiofrequency energy to tissue to create tissue lesions without ablating tissue.

BACKGROUND OF THE INVENTION

The gastrointestinal (GI) tract, also called the alimentary canal, is a long tube through which food is taken into the body and digested. The alimentary canal begins at the mouth, and includes the pharynx, esophagus, stomach, small and large intestines, and rectum. In human beings, this passage is about 30 feet (9 meters) long.

Small, ring-like muscles, called sphincters, surround portions of the alimentary canal. In a healthy person, these muscles contract or tighten in a coordinated fashion during eating and the ensuing digestive process, to temporarily close off one region of the alimentary canal from another region of the alimentary canal.

For example, a muscular ring called the lower esophageal sphincter (or LES) surrounds the opening between the esophagus and the stomach. Normally, the lower esophageal sphincter maintains a high-pressure zone between fifteen and thirty mm Hg above intragastric pressures inside the stomach.

In the rectum, two muscular rings, called the internal and external sphincter muscles, normally keep fecal material from leaving the anal canal. The external sphincter muscle is a voluntary muscle, and the internal sphincter muscle is an involuntary muscle. Together, by voluntary and involuntary action, these muscles normally contract to keep fecal material in the anal canal.

Dysfunction of a sphincter in the body can lead to internal damage or disease, discomfort, or otherwise adversely affect the quality of life. For example, if the lower esophageal sphincter fails to function properly, stomach acid may rise back into the esophagus. Heartburn or other disease symptoms, including damage to the esophagus, can occur. Gastrointestinal reflux disease (GERD) is a common disorder, characterized by spontaneous relaxation of the lower esophageal sphincter.

Damage to the external or internal sphincter muscles in the rectum can cause these sphincters to dysfunction or otherwise lose their tone, such that they can no longer sustain the essential fecal holding action. Fecal incontinence results, as fecal material can descend through the anal canal without warning, stimulating the sudden urge to defecate. The physical effects of fecal incontinence (i.e., the loss of normal control of the bowels and gas, liquid, and solid stool leakage from the rectum at unexpected times) can also cause embarrassment, shame, and a loss of confidence, and can further lead to mental depression.

In certain surgical systems, radiofrequency energy is applied to tissue at different tissue levels to create multiple tissue lesions. Application of such energy requires continuous monitoring of certain tissue and/or device parameters to ensure that the tissue is not heated to such extent that damaging burning of tissue occurs. Thus, these systems monitor tissue temperature and/or device electrode temperature and provide safety features to cut off energy flow if the tissue temperature rises too high. However, with the application of radiofrequency energy, there is a fine point in which tissue is treated to form lesions and beneficially alter structure of the tissue, e.g., alter the structure of the sphincter muscle, while not being ablated.

Ablation of tissue can be generally defined as a removal of a part of tissue. Radiofrequency energy to ablate tissue has been used for various tumor treatments, destroying tissue and creating tissue necrosis. However, avoiding tissue ablation may be beneficial in treating the gastrointestinal tract in the foregoing or other procedures. Therefore, it would be advantageous to provide a system of applying radiofrequency energy to tissue at a power setting and time duration which causes thermal effect to tissue to create tissue lesions along a series of tissue levels but avoids ablation or burning of tissue.

However, in avoiding tissue ablation, care needs to be taken to ensure that tissue is not undertreated. In other words, in attempts to prevent overheating of tissue which causes ablation, the system needs to conversely ensure that tissue is not under-heated and thus not therapeutically treated. Therefore, the need exists for a system that applies radiofrequency energy to tissue between these two energy levels.

SUMMARY OF THE INVENTION

The present invention advantageously provides an electrosurgical system that applies radiofrequency energy to tissue to create tissue lesions at different tissue levels and alters the structure of the tissue, e.g., the sphincter muscle, without ablating or burning the tissue, while on the other hand reducing the incidence of tissue undertreatment. That is, the present invention advantageously provides such electrosurgical system that avoids such overheating of tissue, while at the same time limiting under-heating of tissue which does not effectively treat tissue. Thus, in striking this balance between the overheating and under heating of tissue, more reliable and consistent tissue treatment is achieved.

This prevention of overtreatment and undertreatment are achieved in various ways. The different aspects utilized to achieve the desired tissue treatment can be implemented alone or in combination with each other.

Thus, the system and method of the present invention advantageously keeps tissue treatment within a target zone to provide a therapeutic effect to tissue, defined as thermally heating tissue above a lower parameter wherein tissue is undertreated and below a tissue ablation threshold wherein tissue is overheated and ablated.

In accordance with one aspect, the present invention provides a device for applying radiofrequency energy for sphincter treatment comprising a flexible outer tube, an expandable basket having a plurality of arms movable from a collapsed position to an expanded position, the arms having an opening, and a plurality of electrodes movable with respect to the arms. The plurality of electrodes are movable from a retracted position to an extended position to extend through the openings in the arms. An advancer is slidably disposed within the outer tube, the plurality of electrodes operably coupled to the advancer such that movement of the advancer advances the plurality of electrodes to the extended position extending through the openings in the arms. An elongated spacer is positioned within the outer tube, the spacer having a central lumen to receive the advancer and to maintain a central position of the advancer. The spacer further has an outer wall with at least one slit formed therein to form a flap for insertion of at least one wire into the spacer.

An actuator can be provided for moving the advancer from a first position to a second position to advance the plurality of electrodes.

In some embodiments, the spacer has a plurality of ribs forming four separate regions, each region having a slit to form a flap. In some embodiments, each region receives a wire. In some embodiments, one of the regions receives an aspiration tube and another of the regions receives an irrigation tube. In some embodiments, the spacer has a rib extending from a wall defining the central lumen to an inner wall of the spacer.

The device can include in some embodiments a proximal ring to clamp the outer tube and spacer at a proximal region of the spacer and/or a distal ring to clamp the outer tube and spacer at a distal region of the spacer.

In some embodiments, the slit is elongated and extends longitudinally along at least a portion of the spacer and the flap is openable progressively to progressively lay the wires(s) within the spacer.

In some embodiments, the spacer defines a first spacer and a second spacer axially spaced from the first spacer, the second spacer having a central lumen longitudinally aligned with the center lumen of the first spacer.

In accordance with another aspect, the present invention provides a device for applying radiofrequency energy for sphincter treatment comprising an outer tube, an expandable basket having a plurality of arms movable from a collapsed position to an expanded position, the arms having an opening, and a plurality of electrodes movable with respect to the arms, the plurality of electrodes movable from a retracted position to an extended position to extend through the openings in the arm. An advancer is slidably disposed within the outer tube, the plurality of electrodes operably coupled to the advancer such that advancement of the advancer advances the plurality of electrodes to the extended position. An elongated spacer is positioned within the outer tube, the spacer having a central lumen to receive the advancer and to maintain a central position of the advancer, the spacer being more rigid than the outer tube such that the outer tube can be formed of a more flexible material than if the spacer was not provided.

An actuator can be provided for moving the advancer from a first position to a second position to move the advancer distally.

In some embodiments, the spacer includes an outer wall having at least one longitudinally extending slit formed therein, the slit being separable to provide access to an interior of the spacer. In some embodiments, the slit provides access for placement of a plurality of wires within the interior of the spacer. In some embodiments, the slit provides access for placement of one or both of an irrigation tube or aspiration tube within the interior of the spacer. The spacer in some embodiments, includes a plurality of transverse ribs to form separate internal regions of the spacer and a plurality of longitudinally slits are formed in the outer wall of the spacer to provide access to each of the internal regions.

In accordance with another aspect, the present invention provides a device for applying radiofrequency energy for sphincter treatment comprising a flexible outer tube, an expandable basket having a plurality of arms movable from a collapsed position to an expanded position, the arms having an opening and a plurality of electrodes movable with respect to the arms, the plurality of electrodes movable from a retracted position to an extended position to extend through a respective opening in the arm. The plurality of electrodes have distal tips, the distal tips being axially aligned when the electrodes are in the extended position and ready for application of energy to tissue. An advancer is slidably disposed within the outer tube, the plurality of electrodes operatively coupled to the advancer such that advancement of the advancer advances the plurality of electrodes to the extended position. An elongated spacer is positioned within the outer tube, the spacer having a central lumen to receive and support the electrode advancer and to maintain a central position of the advancer during bending of the outer tube to maintain the axially aligned distal position of the distal tips of the plurality of electrodes such that tissue can be treated without overheating tissue to avoid ablation of tissue.

An actuator can be provided for moving the advancer from a first position to a second position to move the advancer distally.

In some embodiments, the spacer includes a plurality of slits forming flaps for loading wires therein.

In some embodiments, the plurality of electrodes include a location feature engageable with an electrode holder to maintain radial spacing of the electrodes. In some embodiments, the arms have an alignment feature engageable with an arm holder to maintain alignment of the arms.

In some embodiments, the location features maintain an equidistant spacing of the distal tips of the electrodes.

In accordance with another aspect, the present invention provides a system for controlling operation of a radiofrequency treatment device to apply radiofrequency energy to tissue to heat tissue to create tissue lesions without ablating the tissue, the system comprising a first treatment device having a plurality of electrodes for applying radiofrequency energy to tissue. The treatment device further includes a spacer to maintain a centered position of the plurality of electrodes, the plurality of electrodes advanceable from the device to penetrate tissue and apply radiofrequency energy, and the spacer positioned in an outer tube and having a separable portion to access an interior of the spacer. A controller is provided including a connector to which the first treatment device is coupled for use. A generator applies radiofrequency energy to the electrodes. The controller further includes an operation system to execute on a display screen a first graphical interface guiding use of the first treatment device, the controller visually prompting a user in a step-wise fashion to perform a process using the connected treatment device of forming a pattern of lesions in a body region in a plurality of axially spaced lesion levels, each lesion level including a plurality of circumferential spaced lesion. The controller controls application of energy so that the tissue is thermally treated to create lesions but preventing thermal treatment beyond a threshold which would ablate the tissue.

In some embodiments, an aspiration tube and an irrigation tube are inserted into the spacer through the separable portion.

In some embodiments, the spacer has a plurality of separable portions for placement of components within different sections of an interior of the spacer.

In accordance with another aspect, the present invention provides a method of treating gastrointestinal reflux disease comprising the steps of:

providing a treatment device having a plurality of electrodes, the electrodes having an engagement feature to maintain the distal tips in axial alignment when advanced from the device, the device further having a spacer with a central lumen to receive an electrode advancer to maintain centering of the advancer within an outer tube of the device during advancement;

applying radiofrequency energy to the plurality of electrodes to thermally treat tissue below a tissue ablation threshold and create a plurality of tissue lesions along axially spaced tissue levels within the upper gastrointestinal tract;

monitoring tissue temperature throughout the procedure; and regulating power ensuring in response to the monitoring step that the tissue temperature does not exceed a predetermined value which would cause tissue ablation and/or tissue necrosis.

In some embodiments, the distal tips of the electrodes are sharp to penetrate a muscle layer in a lower esophageal sphincter of a patient. In some embodiments, the distal tips of the electrodes are maintained by the engagement feature in an equidistant spaced relationship.

In accordance with another aspect, the present invention provides a method of manufacturing a device for treating body tissue comprising providing an outer tube, providing a spacer, forming at least one longitudinally extending slit in the spacer, and separating the at least one slit to insert at least one wire into the spacer.

In some embodiments, the method further includes the step of separating at least one slit to insert an irrigation tube and aspiration tube into the spacer.

In some embodiments, the spacer includes a plurality of slits, and the method further comprises of the step of separating the plurality of slits to insert wires and tubes into different sections of the spacer.

In accordance with another aspect, the present invention provides a device for applying radiofrequency energy for sphincter treatment comprising a flexible outer tube, an expandable basket having a plurality of arms movable from a collapsed position to an expanded position, the arms having an opening and a plurality of electrodes movable with respect to the arms. The plurality of electrodes are movable from a retracted position to an extended position to extend through the openings in the arms, each of the plurality of electrodes having a first engagement structure. An electrode holder has a second engagement structure to cooperate with the first engagement structure to maintain the electrodes in a desired radial spaced position. An advancer is slidably disposed within the outer tube, the plurality of electrodes operably coupled to the advancer such that movement of the advancer advances the electrodes to the extended position extending through the openings in the arms.

An actuator can be provided for moving the advancer from a first position to a second position to advance the electrodes.

In some embodiments, the first and second engagement structures maintain the electrodes in longitudinal alignment so that distalmost tips of the electrodes terminate at a longitudinally aligned position.

In some embodiments, the device includes a retaining sleeve positioned over the electrode and electrode holder. In some embodiments, the electrode holder has a plurality of elongated receiving areas, each receiving area dimensioned to receive one of the electrodes.

In some embodiments, each of the electrodes terminates in a penetrating tip, the penetrating tips being longitudinally aligned in the retracted position of the electrodes.

In some embodiments, the arms have a basket holder engagement structure engageable with an arm engagement structure on the basket holder to maintain a desired radial spaced position of the arms.

In some embodiments, the arm engagement structure includes one of a plurality of grooves or plurality of projections.

In some embodiments, one of the first or second engagement structure includes a plurality of projections and the other engagement structure includes a plurality of grooves.

In accordance with another aspect, the present invention provides a device for applying radiofrequency energy for sphincter treatment comprising a flexible outer tube, an expandable basket at a distal portion of the device, the basket having a plurality of arms movable from a collapsed position to an expanded position to dilate tissue contacted by the arms of the basket, the arms having an opening. A plurality of electrodes having penetrating tips are movable with respect to the arms. The plurality of electrodes are movable from a retracted position within the arms to an extended position so the penetrating tips of the electrodes extend through the openings in the arms. Each of the electrodes has an engagement structure to maintain the penetrating tips in axial alignment in the retracted position and to maintain a desired radial spacing of the electrodes in the retracted position, wherein upon movement of the electrodes from the retracted to the extended position causing the penetrating tips to extend through openings in the arms, the engagement structure maintains the radial spacing of the electrodes and axial alignment of the penetrating tips in the extended position such that application of radiofrequency energy to tissue is provided in consistent and uniform manner to prevent overheating of tissue and thereby prevent ablation of tissue.

In some embodiments, the device further includes an electrode holder having an engagement structure to cooperate with the engagement structure of the electrodes. The device in some embodiments further includes a retaining sleeve positioned over the electrodes to retain the electrodes within the electrode holder.

In some embodiments, the device further comprises a basket holder, and the arms haves a basket holder engagement structure engageable with structure on the basket holder to locate the arms on the basket holder to maintain the arms in a desired radial spacing to provide consistent spacing when the basket is moved to the expanded position to maintain the desired spacing of the electrodes when in the extended position.

In accordance with another aspect, the present invention provides a device for applying radiofrequency energy for sphincter treatment comprising a flexible outer tube, an expandable basket having a plurality of arms movable from a collapsed position to an expanded position, the arms having an opening and a location feature, and a basket holder having an arm receiving structure wherein engagement of the location feature of the arms and receiving structure of the basket holder maintains a desired radial spacing of the arms in the collapsed position and in the expanded position. A plurality of electrodes are movable with respect to the arms, the plurality of electrodes movable from a retracted position to an extended position to extend through the openings in the arms. An advancer is slidably disposed within the outer tube, the plurality of electrodes operably coupled to the advancer such that movement of the advancer advances the electrodes to the extended position extending through the openings in the arms.

An actuator can be provided to move the advancer from a first position to a second position to advance the electrodes.

In some embodiments, the arm receiving structure includes one of a plurality of projections or plurality of grooves and the location feature on the arms includes one of a plurality of projections or plurality of grooves.

In some embodiments, the basket holder has a lumen to receive an aspiration tube and a balloon inflation tube. In some embodiments, the basket holder has a plurality of arm receiving areas equidistantly spaced.

In some embodiments, each of the arms comprises first, second and third tubes, the first tube receiving one of the electrodes, the second tube receiving a wire and the third tube receiving irrigation fluid.

In accordance with another aspect, the present invention provides a method of treating tissue by applying non-ablative radiofrequency energy comprising the steps of:
 a. providing a device having a plurality of electrodes movable between a retracted position and an extended position, the plurality of electrodes having structure to maintain an equidistant radial spacing and to maintain longitudinal alignment of penetrating tips of the electrodes in the retracted position;
 b. inserting the device into the sphincter of a patient;
 c. advancing the electrodes to penetrate sphincter tissue at a first location, the electrodes having penetrating tips longitudinally aligned in the advanced position and further being equidistantly radially spaced in the advanced position;
 d. applying radio frequency energy to the electrodes to apply radiofrequency energy to tissue in the area of the penetrating tips of the electrodes, the energy applied so a minimum distance is maintained between regions of tissue treated by the electrodes;
 e. retracting the electrodes within the device;
 f. rotating the device to a second position;
 g. advancing the electrodes from the device so that the penetrating tips penetrate sphincter tissue at a second location, the penetrating tips of the electrodes being longitudinally aligned and maintained in an equidistant radial spacing; and
 h. applying radiofrequency energy to the electrodes to apply radiofrequency energy to tissue in the area of the penetrating tips of the electrodes, such fixed radial spacing and longitudinal alignment maintain the minimum distance between the regions of tissue treated to avoid overlapping of tissue treatment area which could cause ablation of tissue.

In some embodiments, the device includes an expandable basket having a plurality of arms, and the method further comprises the step of expanding the basket to dilate the sphincter, the arms having structure to maintain a desired radial spacing of the arms in a non-expanded position and in an expanded position of the basket.

In some embodiments, each penetrating tip has a defined treatment area and the structure by maintaining the radial spacing avoids undertreatment of tissue which could otherwise occur if the penetrating tips were not equidistantly spaced and the electrodes applied energy after rotation of the device to the second position.

In some embodiments the device includes an advancer slidably disposed within an outer tube of the device, the plurality of electrodes operably coupled to the advancer such that movement of the advancer advances the electrodes to the extended position.

Further features and advantages of the inventions are set forth in the following Description and Drawings, as well as in the appended claims.

BRIEF DESCRIPTION OF THE DRAWINGS

FIG. 7 is an isometric view of the spacer of the present invention;

FIG. 8A is front view of the spacer of FIG. 7 shown with the wires positioned therein;

FIG. 9 is a side perspective view of the spacer of FIG. 7 showing the wires being inserted into the spacer during a manufacturing step;

FIGS. 10 and 11 are isometric and side cross-sectional views, respectively, of the spacer OF FIG. 7;

FIG. 12 is a side view of an alternate embodiment of the spacer of the present invention;

FIG. 19 is a side view of the needle electrode of the present invention;

FIG. 20 is a top view of the needle electrode of FIG. 19;

FIG. 27 is a top view of one of the basket arms (spines);

FIG. 28 is an enlarged view of the area of detail identified in FIG. 27;

FIG. 29 is a bottom view of the basket arm of FIG. 27;

FIGS. 35A and 35B illustrate what occurs if the needle electrode tips are not radially aligned;

FIG. 35C illustrates what occurs if the needle electrode tips are not longitudinally aligned;

FIGS. 36-38 illustrate the method of use of the device of FIG. 2A wherein

FIG. 36 shows the device inserted within a sphincter in the non-expanded condition;

FIG. 37 shows the basket expanded to dilate the sphincter wall, and FIG. 38 shows the needle electrodes deployed to penetrate tissue.

Figure 1A:
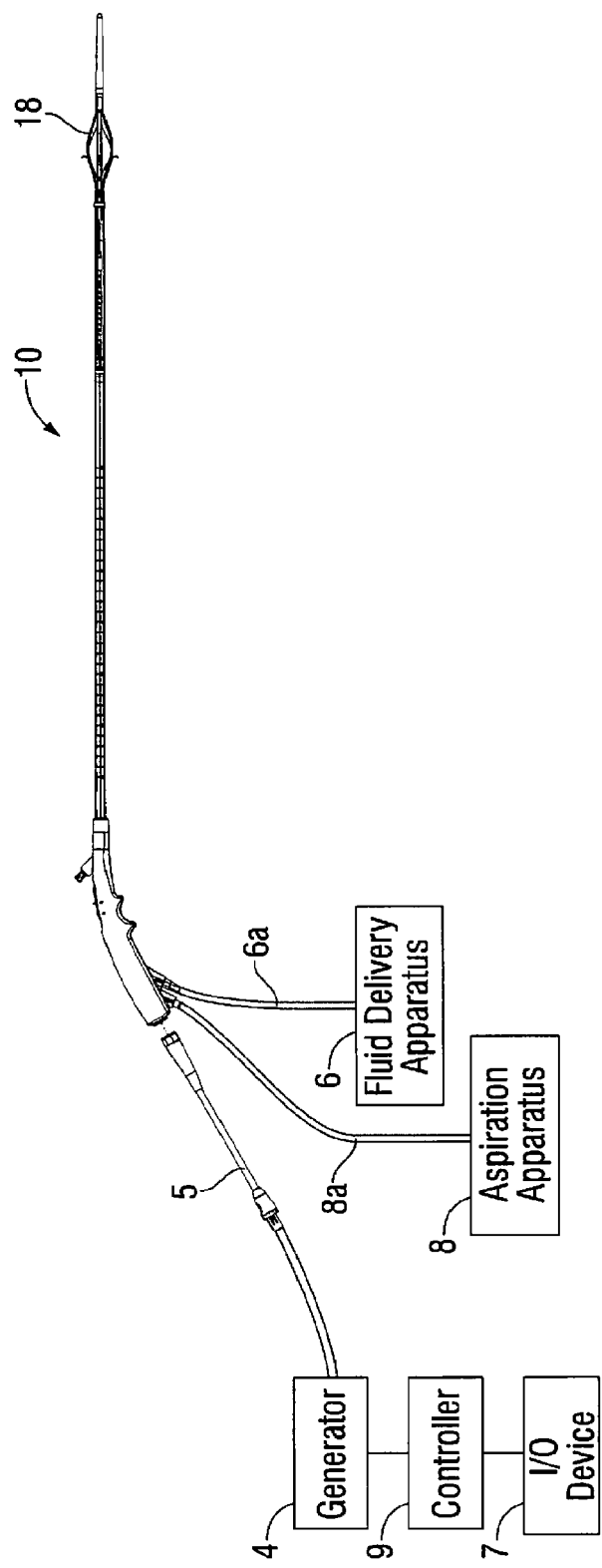
FIG. 1A is a schematic view of one embodiment of a system for use with the device of the present invention.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF PREFERRED EMBODIMENTS

This specification discloses various systems and methods for treating dysfunction of sphincters and adjoining tissue regions in the body. The systems and methods are particularly well suited for treating these dysfunctions in the upper gastrointestinal tract, e.g., gastro-esophageal reflux disease (GERD) affecting the lower esophageal sphincter and adjacent cardia of the stomach. For this reason, the systems and methods will be described in this context. Still, it should be appreciated that the disclosed systems and methods are applicable for use in treating other dysfunctions elsewhere in the body, including dysfunctions that are not necessarily sphincter-related. For example, the various aspects of the invention have application in procedures requiring treatment of hemorrhoids, or fecal incontinence, or urinary incontinence, or restoring compliance to or otherwise tightening interior tissue or muscle regions. The systems and methods that embody features of the invention are also adaptable for use with systems and surgical techniques that are catheter-based and not necessarily catheter-based.

The systems and methods disclosed herein provide application of radiofrequency energy to tissue via a plurality of electrodes. The energy is applied via the electrodes to tissue at a series of axially spaced tissue levels, thereby forming tissue lesions which alters the tissue structure. Prior application of radiofrequency energy to tissue in various surgical procedures involved application of energy at certain levels and for a certain period of time with the goal to ablate the tissue. That is, the objective was to cause tissue necrosis and remove tissue. The systems and methods of the present disclosure, however, treat tissue without ablating the tissue and without causing tissue necrosis, which advantageously achieves better clinical results, especially when treating the sphincter muscles of the GI tract in the specific surgical procedures disclosed herein. By applying sufficient energy to cause thermal effect to tissue, but without ablating or burning the tissue, tissue reconstruction/remodeling occurs which results in beneficial changes to tissue properties, thus beneficially treating GERD which is caused by the spontaneous relaxation of the lower esophageal sphincter and beneficially treating fecal incontinence caused by loss of tone of the sphincter muscles in the anal canal. The system of the present disclosure rejuvenates muscle to improve muscle function. The system of the present invention also increases the smooth muscle/connective ratio which results in sphincter reinforcement and remodeling.

In studies performed, it was found that application of non-ablative RF energy to sphincter muscle influences the structural arrangement of smooth muscle and connective tissue contents. The increase of the smooth muscle fibers area per muscle bundles as well as the collagen and myofibroblast contents within the internal anal sphincter were found to be potentially responsible for sphincter reinforcement and remodeling. More specifically, in studies, it was found that application of non-ablative RF energy increased smooth muscle/connective tissue ratio without changes (increase) in the collagen I/III ratio. There was an increase in diameter and number of type I fibers in the external anal sphincter after non-ablative RF and higher cellular smooth muscle content in the internal anal sphincter, suggesting that sphincter remodeling by non-ablative RF energy resulted from activation and repopulation of smooth muscle cells, possibly related to phenotype switch of fibroblasts into myofibroblasts and external anal sphincter fibers. In one animal study, quantitative image analysis showed the cross-section occupied by smooth muscle within the circular muscle increased by up to 16% after non-ablative RF, without increase in collagen I/III ratio, and external anal sphincter muscle fiber type composition showed an increase in type I/III fiber ratio from 26.2% to 34.6% after non-ablative RF, as well as a 20% increase in fiber I type diameter compared to controls.

For such aforedescribed non-ablation RF treatment, the system and method of the present disclosure ensure proper radial and longitudinal (axial) alignment of the tips of the needle electrodes. This can prevent overheating of tissue since the equidistantly spaced electrodes ensure there is no undesired overlap of tissue treatment regions which could occur if the tips were not equally radially spaced. This is especially the case since the device in use is rotated to treat lesions at the same axial lesion level and moved longitudinally to treat tissue at different axial lesion levels. Such radial spacing and longitudinal alignment also ensures that tissue is not undertreated which could occur if spacing between the needle tips is too great and therefore areas of tissue are not properly treated. Furthermore, the longitudinal spacing ensures that tissue is not overheated or underheated due to undesired variations of tissue penetration/depth of energy application, compounded due to rotation and longitudinal repositioning of the device. This is discussed in more detail below.

Various features of the surgical treatment devices connected to the controller achieve the foregoing. Preventing overheating of tissue is achieved by enhanced control of tissue treatment areas and enhanced temperature control of the tissue, which is accomplished in one way by more accurate needle tip alignment, more accurate basket alignment, and/or maintaining centering of the needle advancer during flexing of the catheter to maintain a desired depth of penetration during bending of the device.

FIG. 1A shows a unified system for diagnosing and/or treating dysfunction of sphincters and adjoining tissue in the body. The targeted sphincter regions can vary. In the illustrated embodiment, one region comprises the upper gastrointestinal tract, e.g., the lower esophageal sphincter and adjacent cardia of the stomach. Other regions are also contemplated.

Figure 2A:
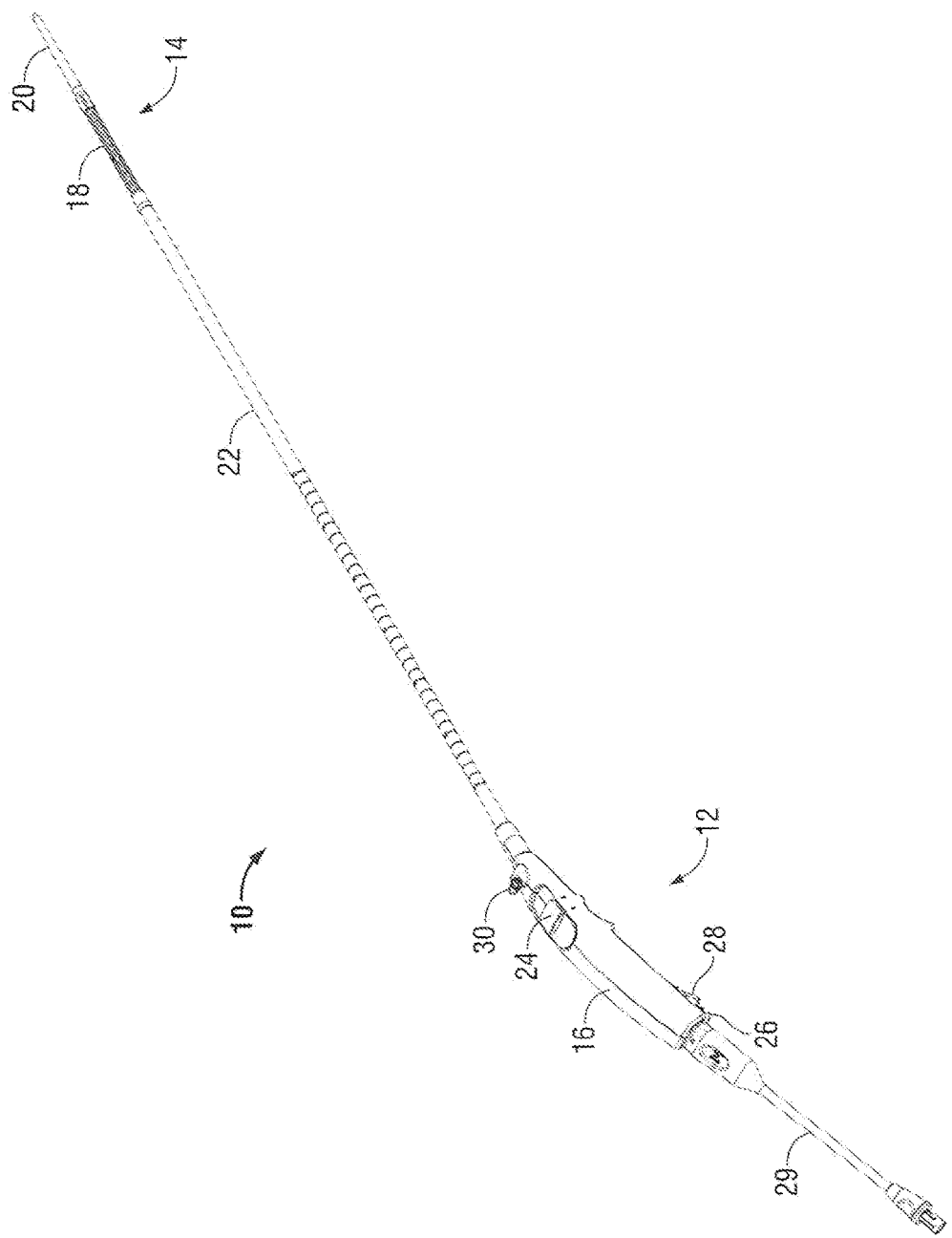
FIG. 2A is an isometric view of a first embodiment of the device of the present invention shown with the basket in the non-expanded position.
Figure 2B:
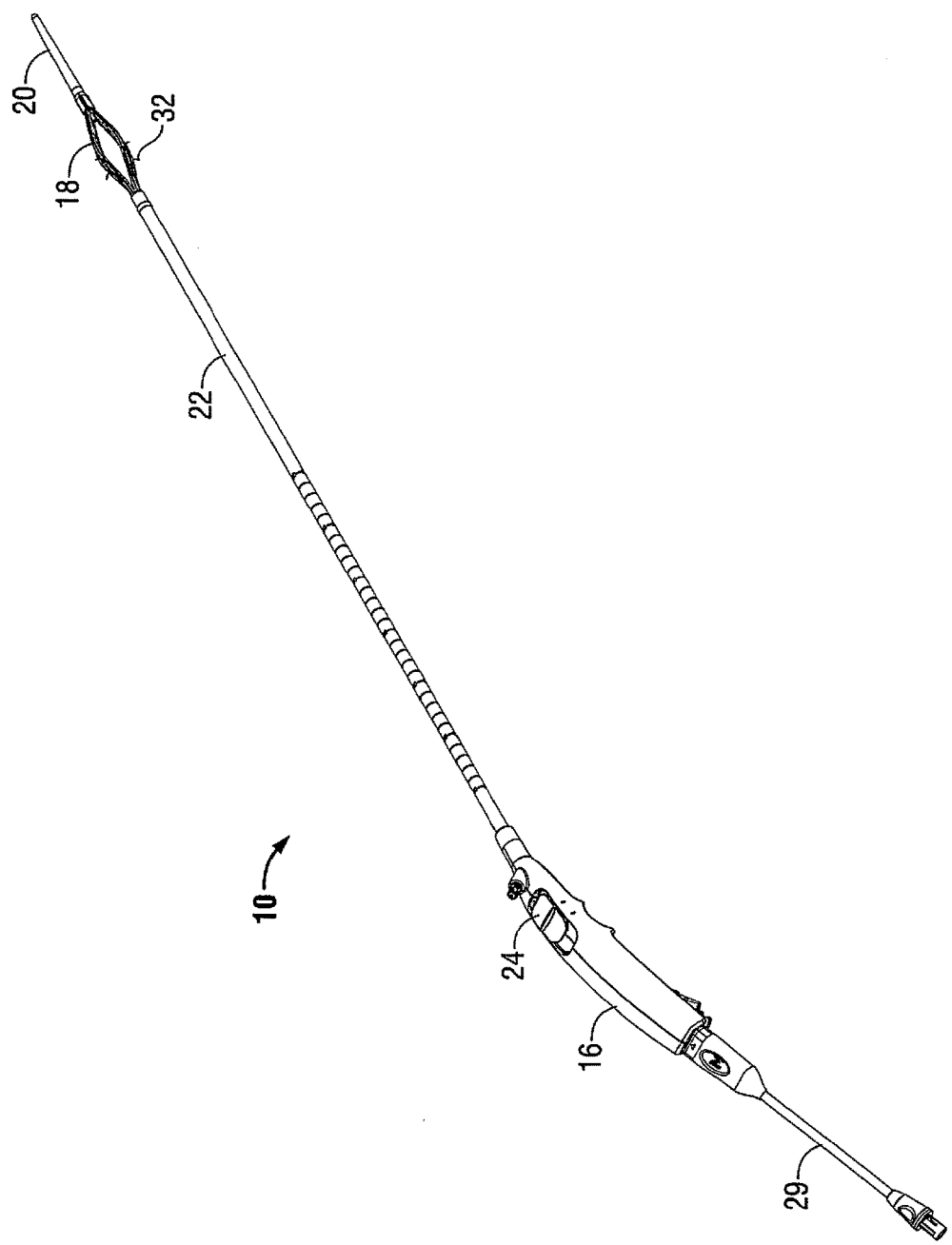
FIG. 2B is an isometric view of the device of FIG. 2A shown with the basket in the expanded position and the electrodes in the advanced (deployed) position.

In the illustrated embodiment, the device 10 of FIGS. 2A and 2B function in the system to apply energy in a selective fashion to tissue in or adjoining the targeted sphincter region. The applied energy creates one or more lesions, or a prescribed pattern of lesions, below the surface of the targeted region without ablating tissue. The subsurface lesions are desirably formed in a manner that preserves and protects the surface against thermal damage. Preferably, the energy is applied to the muscle layer, beyond the mucosa layer.

Natural healing of the subsurface lesions leads to a reconstruction/remodeling of the tissue which leads to beneficial changes in properties of the targeted tissue. The subsurface lesions can also result in the interruption of aberrant electrical pathways that may cause spontaneous sphincter relaxation. In any event, the treatment can restore normal closure function to the sphincter region as the non-ablating application of radiofrequency energy beneficially changes the properties of the sphincter muscle wall. Such energy rejuvenates the muscle to improve muscle function.

With reference to FIG. 1A, the system 2 includes a generator 4 to supply the treatment energy to the device 10. In the illustrated embodiment, the generator 4 supplies radio frequency energy, e.g., having a frequency in the range of about 400 kHz to about 10 mHz, although other ranges are contemplated. Other forms of energy can be applied, e.g., coherent or incoherent light, heated or cooled fluid, resistive heating, microwave, ultrasound, a tissue ablation fluid, or cryogenic fluid. Device 10 is coupled to the generator 4 via a cable connector 5 to convey the generated energy to the respective device 10.

The system preferably also includes certain auxiliary processing equipment. In the illustrated embodiment, the processing equipment includes an external fluid delivery apparatus 6 and an external aspiration apparatus 8.

Device 10 can be connected via tubing 6a to the fluid delivery apparatus 6 to convey processing fluid for discharge by or near the device 10. Device 10 can also be connected via tubing 8a to the aspirating apparatus 8 to convey aspirated material by or near the device for removal.

The system also includes a controller 9. The controller 9, which preferably includes a central processing unit (CPU), is linked to the generator 4, and can be linked to the fluid delivery apparatus 6, and the aspiration apparatus 8. Alternatively, the aspiration apparatus 8 can comprise a conventional vacuum source typically present in a physician's suite, which operates continuously, independent of the controller 9.

The controller 9 governs the power levels, cycles, and duration that the radio frequency energy is distributed to the device 10 to achieve and maintain power levels appropriate to achieve the desired treatment objectives. In tandem, the controller 9 also desirably governs the delivery of processing fluid and, if desired, the removal of aspirated material. Thus, the controller maintains the target tissue temperature to ensure the tissue is not overheated.

The controller 9 includes an input/output (I/O) device 7. The I/O device 7 allows the physician to input control and processing variables, to enable the controller to generate appropriate command signals. The I/O device 7 also receives real time processing feedback information from one or more sensors associated with the operative element of the device (as will be described later), for processing by the controller 9 e.g., to govern the application of energy and the delivery of processing fluid. The I/O device 7 also includes a graphical user interface (GUI), to graphically present processing information to the physician for viewing or analysis.

Figure 1B:
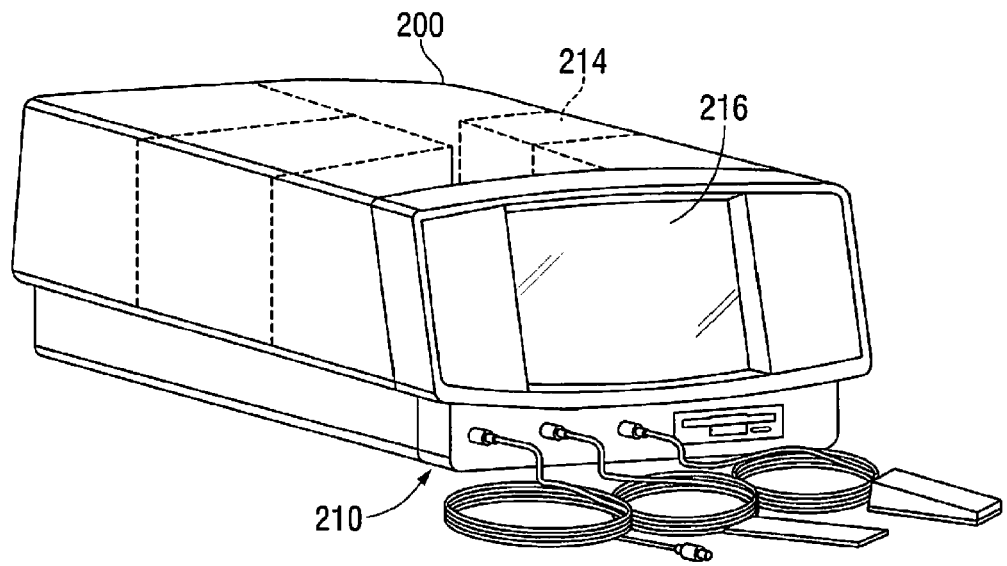
FIG. 1B is a perspective view of one embodiment of an integrated device incorporating features of the system shown in FIG. 1.

In an alternate embodiment of FIG. 1B, the radio frequency generator, the controller with I/O device, and the fluid delivery apparatus (e.g., for the delivery of cooling liquid) are integrated within a single housing 200. The I/O device 210 couples the controller to a display microprocessor 214. The display microprocessor 214 is coupled to a graphics display monitor 216 in the housing 200. The controller 212 implements through the display microprocessor 214 the graphical user interface, or GUI, which is displayed on the display monitor 216. The graphical user interface can be realized with conventional graphics software using the MS WINDOWS® application. The GUI is implemented by showing on the monitor 216 basic screen displays.

Figure 1C:
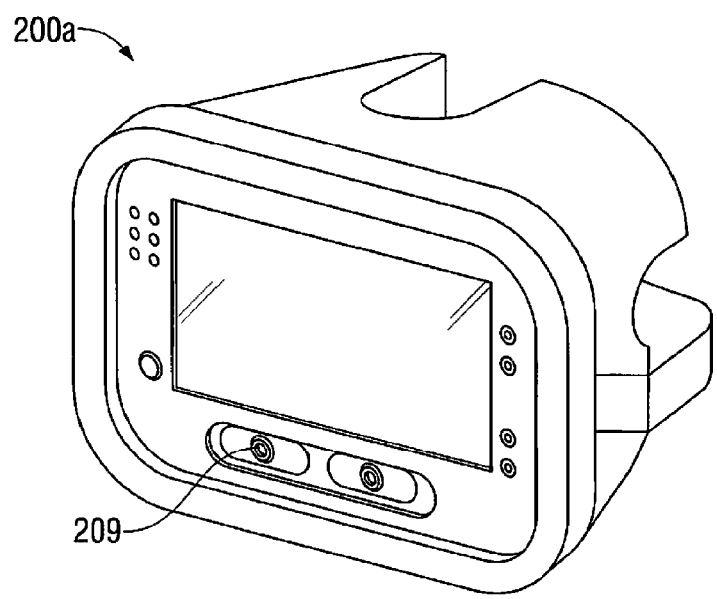
FIG. 1C is a perspective view of an alternate embodiment of an integrated device incorporating features of the system shown in FIG. 1.

FIG. 1C illustrates another embodiment where the radio frequency generator, the controller with I/O device, and the fluid delivery control apparatus (e.g., for the delivery of cooling liquid) are integrated within a single housing 200a. Connection port 209 is for connecting the treatment device.

Turning now to the treatment device of the present invention, in general, the device 10 is a catheter-based device for treating sphincter regions in the upper gastrointestinal tract, and more particularly, the lower esophageal sphincter and adjoining cardia of the stomach to treat GERD. In the embodiment shown, the device 10 includes a flexible catheter tube 22 that has a handle 16 at its proximal end. The distal end of the catheter tube 22 carries the operative element. Note that for clarity throughout the drawings not all identical components are labeled in the specific drawing.

With reference to FIGS. 2A-4, wherein like reference numerals refer to like parts throughout the several views, device 10 has a proximal portion 12, a distal portion 14 and an elongated flexible outer catheter tube 22. Contained within the outer tube 22 is spacer 40 discussed in more detail below. The basket assembly is designated generally by reference numeral 18 and is movable between a collapsed position (configuration) to provide a reduced profile for delivery and an expanded position (configuration) to dilate the tissue, e.g., the sphincter wall. The basket assembly 18 includes a balloon 80 (FIG. 4) which is inflated via inflation portion 30 extending from handle 16 to expand the basket 18.

Also extending from handle 16 is an aspiration port 26 to enable aspiration through the device 10 and an irrigation port 28 to enable fluid injection through the device 10.

The device 10 also includes a plurality of needle electrodes 32 which are movable from a retracted position for delivery to an advanced position protruding through the basket for penetrating tissue. Plug 29 extends from handle 16 and electrically communicates with a generator to apply radiofrequency to the electrodes 32 for application of such energy to treat tissue as discussed in more detail below. Slider 24 on handle 16 is one type of mechanism (actuator) that can be used to advance the needle electrodes 32. In this mechanism, slider 24 is movable from an initial position of FIG. 2A to a second advanced position of FIG. 2B to advance the electrodes 32. Such advancement is achieved as rod 33 (FIG. 3) is attached to the slider 24 at one end and the other end is attached to needle pusher 42. A proximal end of the needle electrodes 32 are coupled to a distal end of the needle pusher (advancer) 42. Rod 33 can include a calibration nut 33a.

As used herein, attached, connected or coupled is not limited to direct attachment, connecting or coupling as interposing components can be used.

Figure 3:
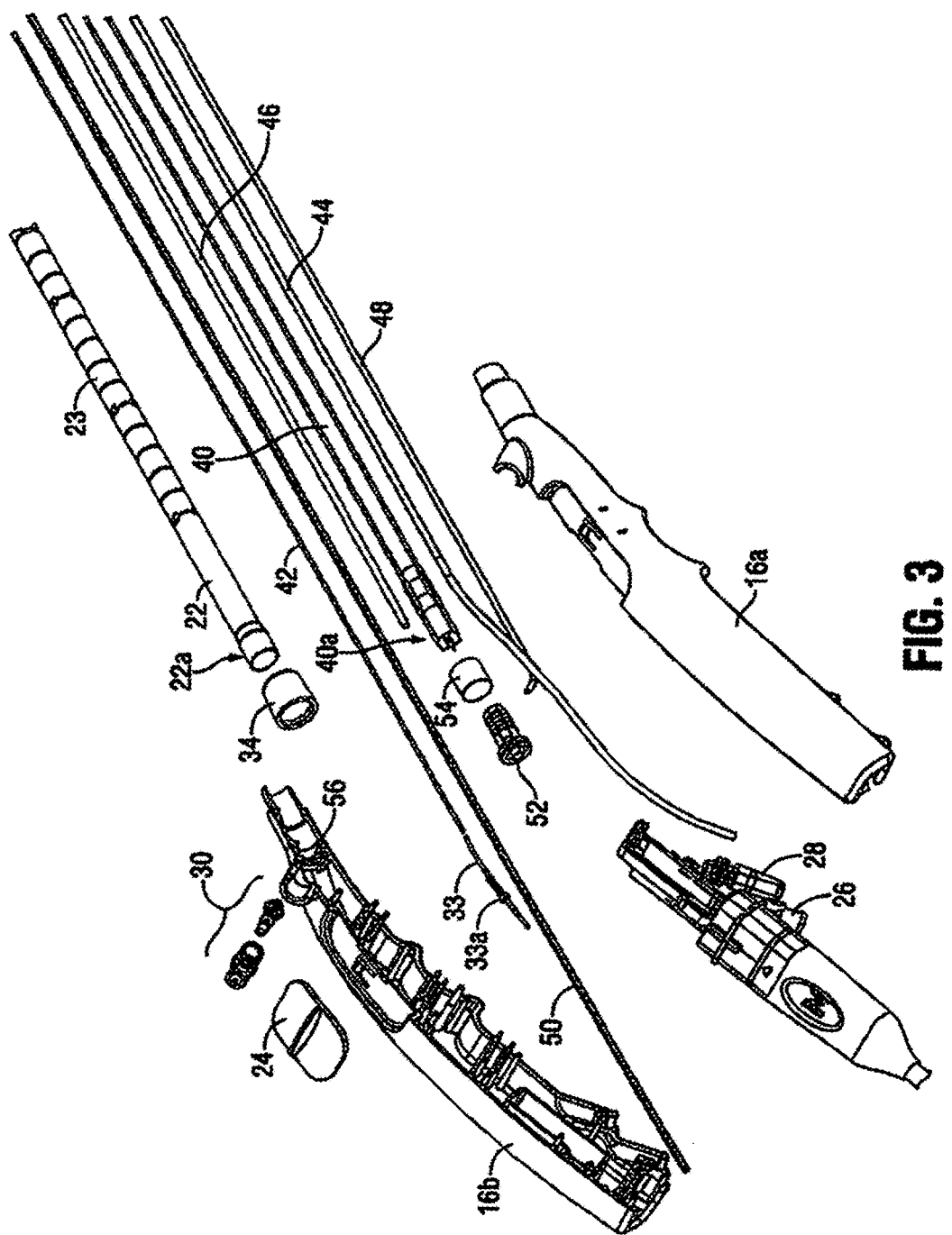
FIG. 3 is an exploded isometric view of the proximal region of the device of FIG. 2A.
Figure 4:
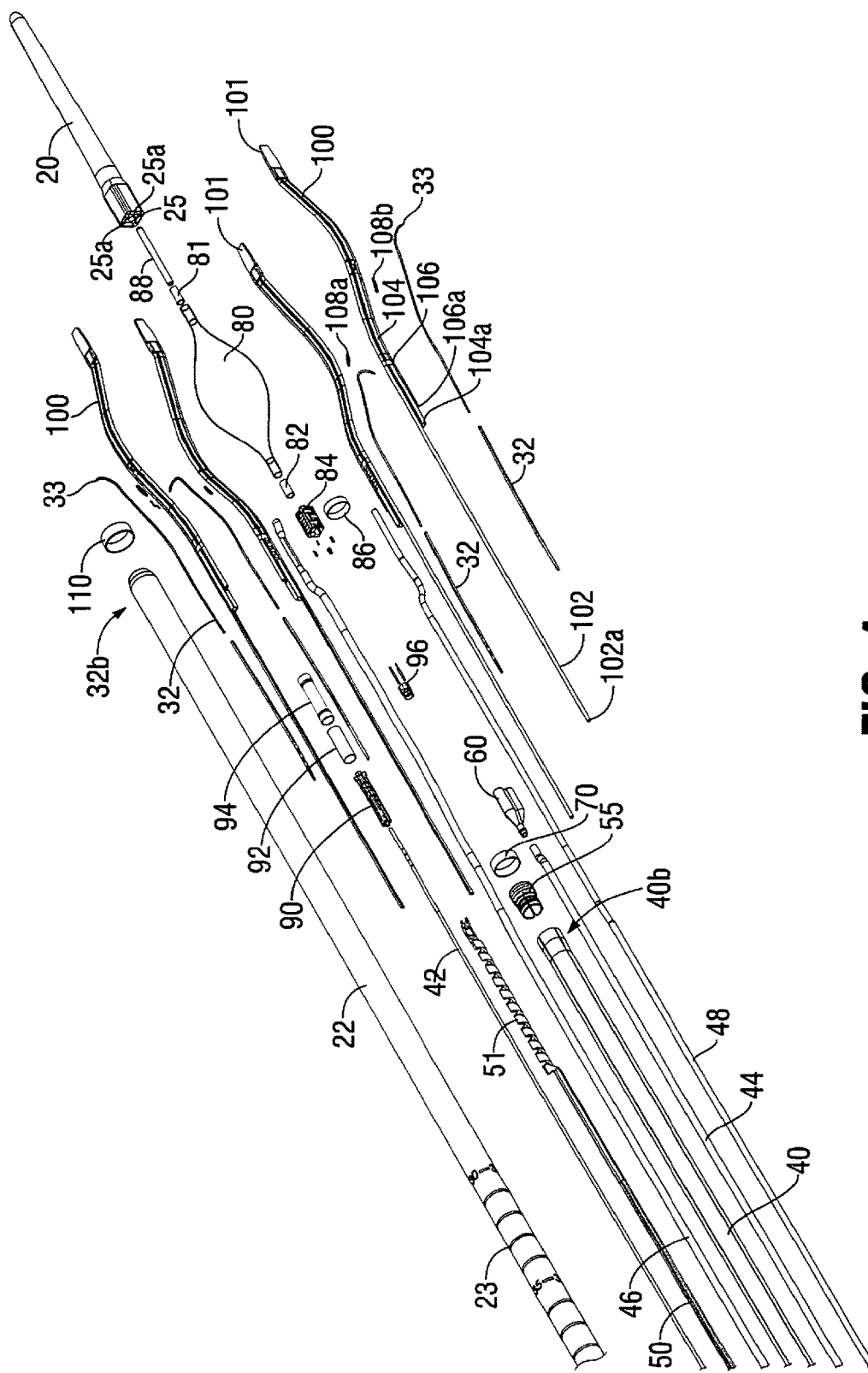
FIG. 4 is an exploded isometric view of the distal region of the device of FIG. 2A.
Figure 5:
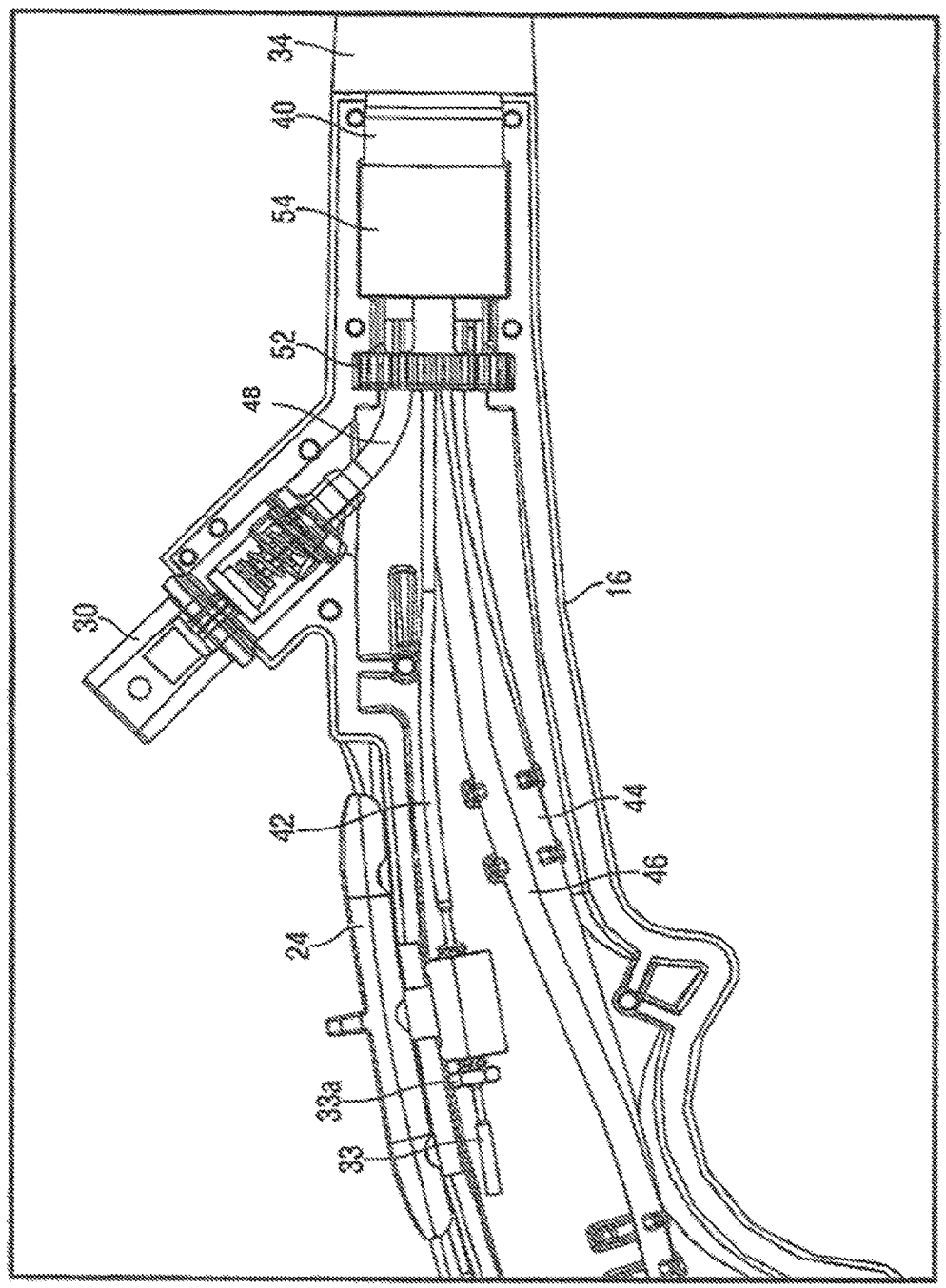
FIG. 5 is a side view with a portion of the housing removed to illustrate the internal components within the handle section and a proximal portion of the spacer with the clamp.
Figure 6:
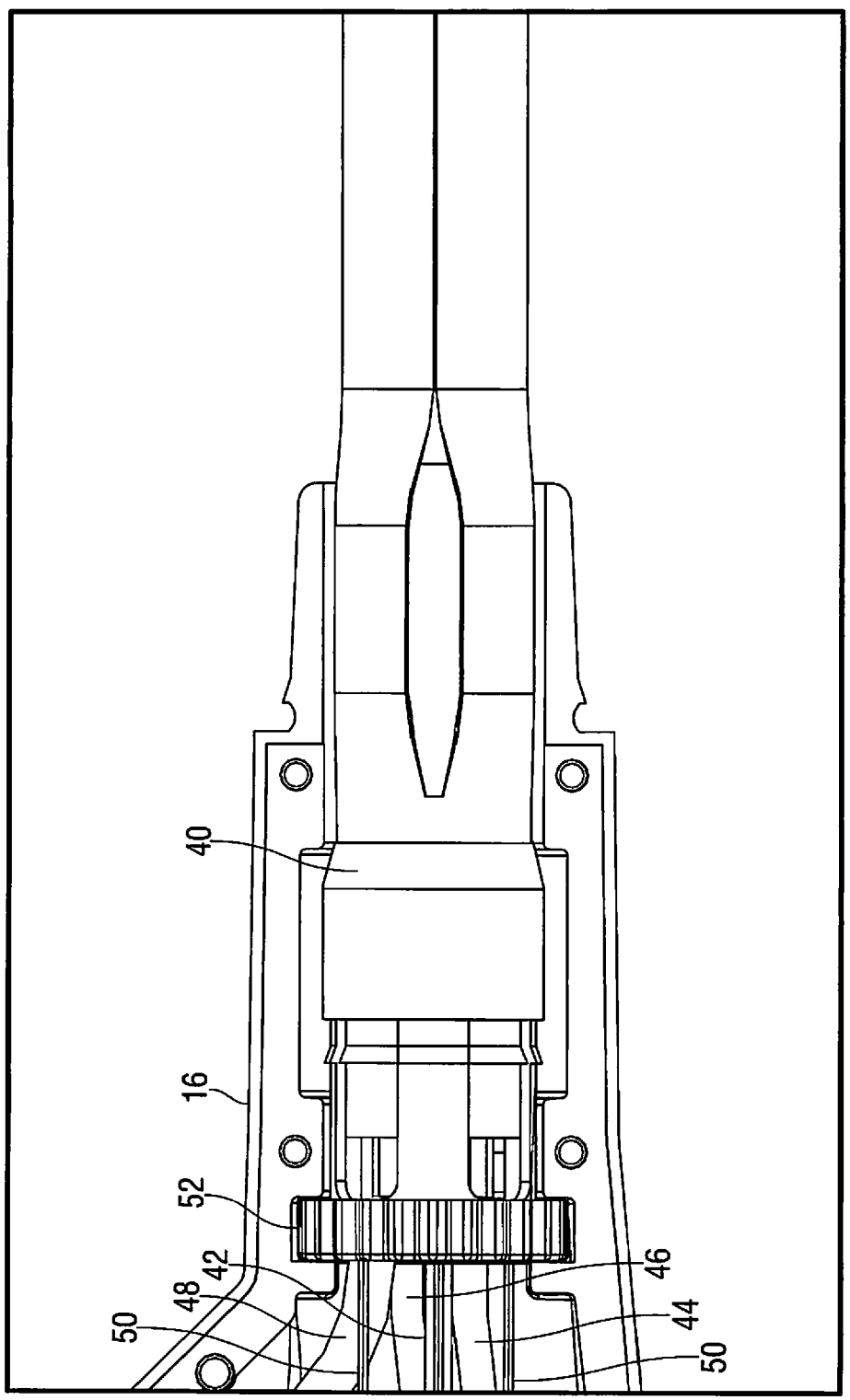
FIG. 6 is a side view of a portion of the housing removed to illustrate the internal components within the handle section and the proximal portion of the spacer, the clamp removed for clarity.

Spacer 40 is positioned within outer tube 22 and functions to separate the various internal components and maintain a center position of needle advancer 42. Needle advancer 42 is slidably positioned within a central lumen of the spacer 40. Also contained within the spacer 40, in various quadrants thereof, which will be discussed in more detail below, are the irrigation tube 44 which fluidly communicates with the irrigation port 28 and the arms of the basket assembly 18 and the aspiration tube 46 which communicates with the aspiration port 26. The aspiration tube 46 opening is positioned proximal of the balloon 80. Inflation tube 48 communicates with inflation port 30 (which receives a syringe) to inflate the balloon 80 contained within the basket assembly 18 and is also positioned within spacer 40. A valve is preferably provided to limit balloon inflation. Wires 50, only a few of which are shown in FIG. 3 for clarity, although in preferred embodiments twelve wires would be provided for the reasons described below, are also positioned within spacer 40. Wire bundle 51 is shown in FIG. 4. Fastener 52 is attached to internal threads 56 of handle 16, with spacer clamp 54 clamping fastener 52 to connect spacer 40 to handle 16 (see also FIG. 5). Note FIG. 6 illustrates the spacer 40 mounted within handle 16 with the clamp 54 removed for clarity.

In the illustrated embodiment (see FIG. 4), at least one temperature sensor is associated with each needle electrode 32. One temperature sensor 108a senses temperature conditions near the exposed distal end of the electrode 32. A second temperature sensor 108b is located on the corresponding spine 100, which rests against the mucosal surface when the balloon structure 80 is inflated to measure temperature of the tissue adjacent the needle electrode 32.

Figure 17:
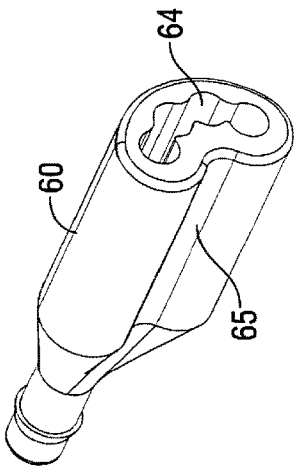
FIGS. 16 and 17 are front and back isometric views, respectively, of the irrigation manifold.
Figure 16:
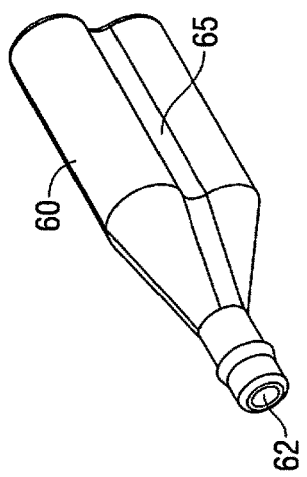
Figure 18:
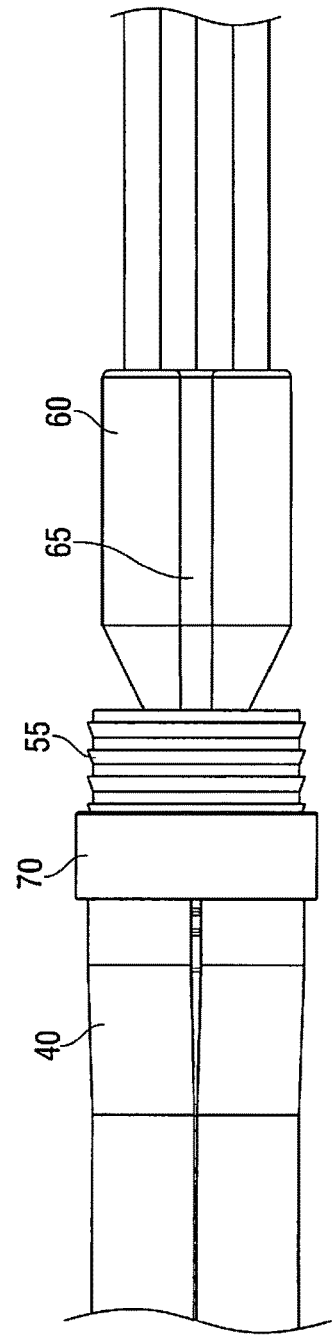
FIG. 18 is a side view of the irrigation manifold of FIG. 16 with the basket arms inserted.
Figure 21:
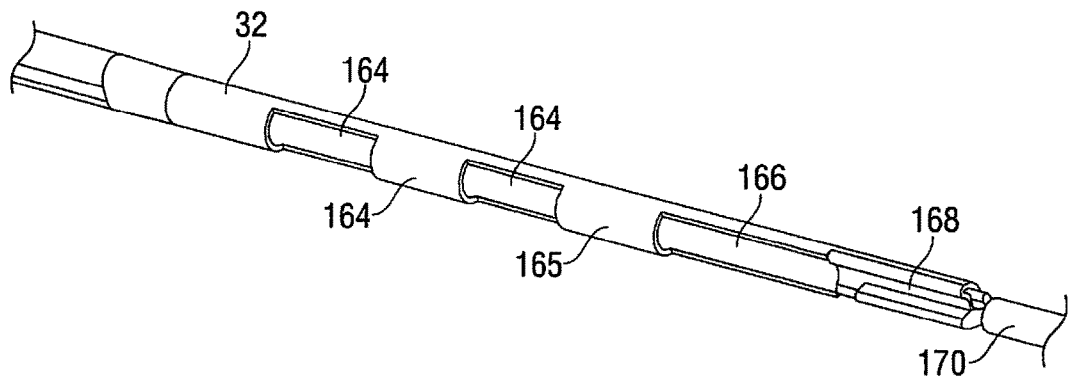
FIG. 21 is an enlarged view of the location feature of the electrode needle of FIG. 19.
Figure 22:
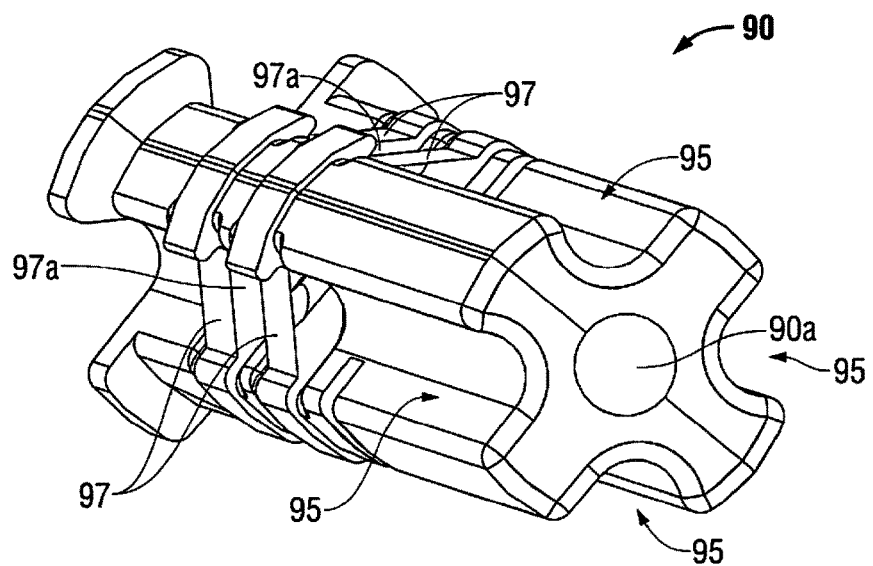
FIG. 22 is an isometric view of the needle holder.

The irrigation tube 44 communicates with manifold 60. As shown in FIGS. 16-18, manifold 60 has an inlet opening 62 which is coupled to the irrigation tube 44 and a plurality of exit openings 64, each communicating with one of the spines 100 of the basket assembly 18. In this manner, fluid entering the manifold 60 through the single inlet opening 62 is subdivided for distribution through each of the four radially spaced spines 100 of the basket assembly 18 for exit through an irrigation opening in each of the spines 100.

With reference to FIG. 4, the basket structure will now be discussed. In the illustrated embodiment, the three-dimensional basket 18 includes one or more spines or arms 100, and typically includes four spines 100, which are held together at a distal end by a distal tip 20 and at proximal end by basket holder 84. In the illustrated embodiment, four spines 100 are shown, spaced circumferentially at 90-degree intervals.

An expandable structure comprising a balloon 80 is located within the basket arms 100. The balloon 80 can be made from various materials such as by way of example, a Polyethylene Terephthalate (PET) material, or a polyamide (non-compliant) material, or a radiation cross-linked polyethylene (semi-compliant) material, or a latex material, or a silicone material, or a C-Flex (highly compliant) material.

The balloon and basket arms are shown in FIG. 2A in a normally, generally collapsed condition, presenting a low profile for delivery into the esophagus.

A balloon tube 82 includes an interior lumen, which communicates with the interior of the balloon 80. A fitting 30 (FIG. 3), such as a syringe-activated check valve, extends from the handle 16 and communicates with the lumen in the inflation tube 48 and the lumen within the balloon tube 82. The fitting 30 couples the lumen to a syringe for injection of fluid under pressure through the lumen into the balloon structure 80, causing its expansion.

Expansion of the balloon 80 urges the basket arms 100 to open and expand to the expanded position (condition) of FIG. 2B. The force exerted by the balloon 80 and arms 100, when expanded, is sufficient to exert an opening or dilating force upon the tissue surrounding the basket arms 100. The balloon 80 can be expanded to varying diameters to accommodate for varying patient anatomy.

As noted above, the basket structure is composed of four basket arms or spines 100. Each spine 100 has three tube or spine sections 102, 104 and 106 (see e.g. FIGS. 4 and 27). The spine 100 can be formed by a tri-lumen extrusion or alternately by separate tubes attached together. Note tube 104 is positioned between tubes 102 and 106 and can have flattened surfaces 104C (FIG. 31), rather than round surfaces of tubes 102, 106, to facilitate manufacture.

Tube 102 has a proximal opening 102a to receive the irrigation tube 44, tube 104 has a proximal opening 104a to receive the needle electrode 32, and tube 106 has a proximal opening 106a to receive the wires for temperature sensors 108a, 108b. As shown, the proximal openings 102a, 104a and 106a are staggered, with the opening 102a being the most proximal, the opening 106a being the most distal and the opening 104a axially intermediate openings 102a and 106a. Tube 102 of spine 100 has an exit opening 102b (FIG. 28) to allow for exit of fluid into the tissue, tube 104 has an exit opening 104b to enable the needle electrode 32 to be angularly deployed from the spine 100, and tube 106 has an opening 106b for the sensor 108.

Balloon 80, positioned within the basket arms 102, 104, 106 has a tube 82 which is mounted within basket holder 84. Basket holder clamp 86 (FIG. 4) fixedly retains spines 100 within basket holder 84 and retains basket holder 84 within outer tube 22. Basket holder clamp 86 is seated within the outer tube 22, and outer clamp 110 is positioned over outer tube 22 and over basket holder clamp 86. Tube extension 88, extending distally from connector tube 81 attached to balloon 80, is connected within the central opening 25 of distal tip 20. The flat ends 101 of basket arms 100 connect within proximal slots 25*a* of distal tip 20.

Figure 30B:
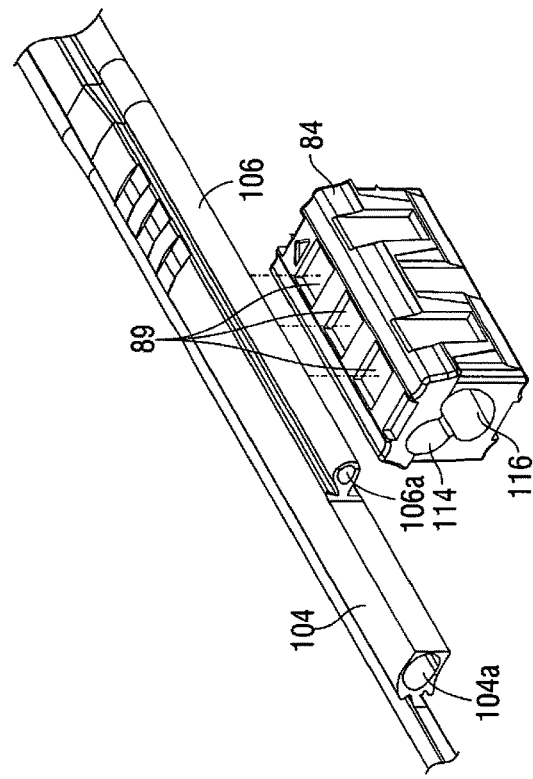
FIG. 30B illustrates the opposing side of the basket arm and basket holder of FIG. 30A.
Figure 30C:
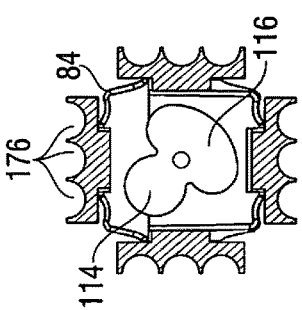
FIG. 30C is a cross-sectional view illustrating an alternate embodiment and showing the four arm channels engaged with the basket holder.
Figure 30A:
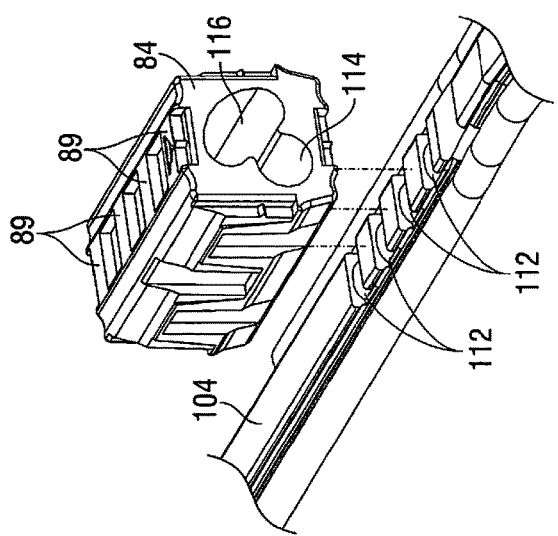
FIG. 30A is an isometric view of one of the basket arms being inserted into the basket holder.
Figure 33:
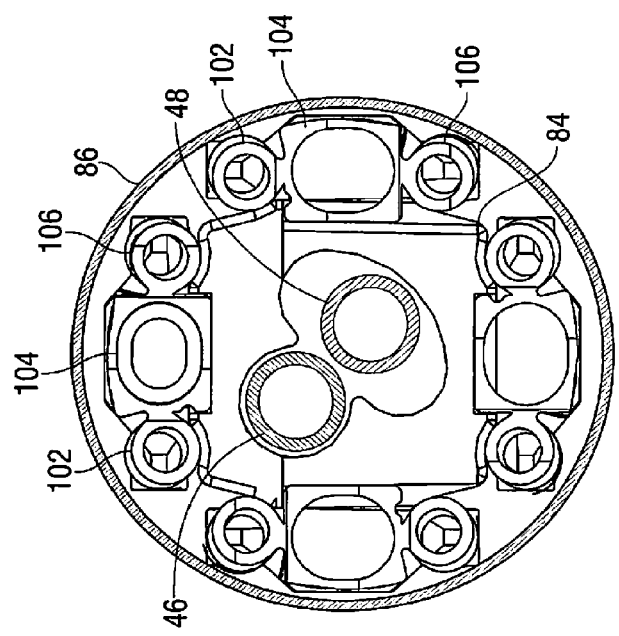
FIG. 33 is a front view showing all four basket arms positioned in the basket holder.
Figure 31:
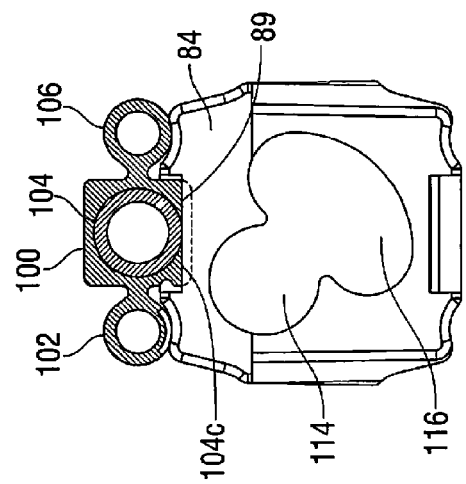
FIG. 31 is a front view in partial cross-section showing the basket arm of FIG. 30A engaged within the basket holder.
Figure 32:
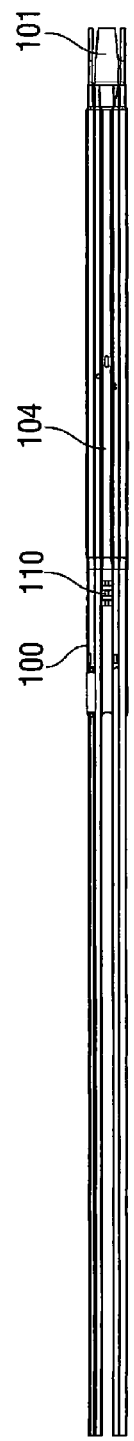
FIG. 32 is a side view showing the basket arms positioned in the basket holder.

With reference to FIGS. 27-32, the basket arms (spines) 100 include a location feature or structure to maintain radial alignment/spacing. In the illustrated embodiment, the location feature includes a series of grooves on the basket arms 100 which cooperate with bumps (or projections) on the basket holder 84 so the arms 100 are maintained in radial alignment with fixed radial spacing. More specifically, a bottom surface of the tube 104 of spine 100 includes a set of four grooves 112. The grooves 110 on the top surface of arms 110 facilitate grasping during manufacture. The grooves 112 receive projections 89 on basket holder 84. That is, the configuration and dimension of the grooves correspond to the configuration and dimensions of the bumps. Thus, this location feature of the arms 100 ensures the arms are properly seated within basket holder 84 to ensure the desired alignment of the arms 100 e.g., equidistant radial spacing, is provided during manufacture and maintained during use. It should be appreciated that this location feature can alternately be configured so the projections are on the arms 100 and the grooves are in the basket holder 84. Other location/alignment engagement features are also contemplated to maintain radial alignment of the basket arms 100. Also, although four projections/grooves are provided in the illustrated embodiment, a different number can be utilized for the engagement structure. The bump/groove engagement can be a location feature which requires a clamp such as clamp ring 86 to maintain the position, or alternatively the location feature can also interlock to frictionally engage. FIG. 31 illustrates a cross-sectional view of one of the spines 100 mounted within the basket holder. Only one of the spines 100 is shown in FIG. 31 for clarity. FIG. 33 is a front view (looking distally from the proximal end) showing all four arms 100 attached thereover to the basket holder 34, with the basket holder clamp ring 86 attached to retain the holder 34 within outer tube 22.

Within basket holder 84 is lumen 114 which receives the aspiration tube 46 and lumen 116 which receives the balloon inflation tube 48.

In an alternate embodiment, U-shaped channels 176 can be provided and circular tubes (not shown) snapped into the channels. This is illustrated in FIG. 30C wherein three separate tubes (not shown) would be snapped into each of the four sets of channels.

Turning now to the needle electrode assembly, the needle pusher (advancer) 42, as noted above, is connected to needle electrodes 32. Pusher 42 is coupled at its distal end to needle holder 90. Holder ring 94 (FIG. 4) is positioned over needle holder 90 and retained by clamping sleeve 92 positioned over holder ring 94. That is, clamping sleeve 92 is positioned over holder clamp 94 and needle holder 90 to fix the needle electrodes 32 within the needle holder 90.

Each spine (basket arm) 100 carries an electrode 32. Therefore, there are four electrodes circumferentially equidistantly spaced at 90-degree intervals. Each electrode 32 is carried within the tubular member or lumen 104 of spine 100 for sliding movement from a retracted position, withdrawn within the spine 100, to an extended position, extending outwardly from the spine 100 (see FIG. 2B) through opening 104*a* in the lumen 104. A sliding actuator 24 (FIGS. 3 and 5) on the handle 16 as described above is coupled to the sliding electrodes 32 so that the actuator 24 controls movement of the electrodes 32 between the retracted position and the extended position (by sliding the actuator from the position of FIG. 2A to the position of FIG. 2B).

Figure 38:
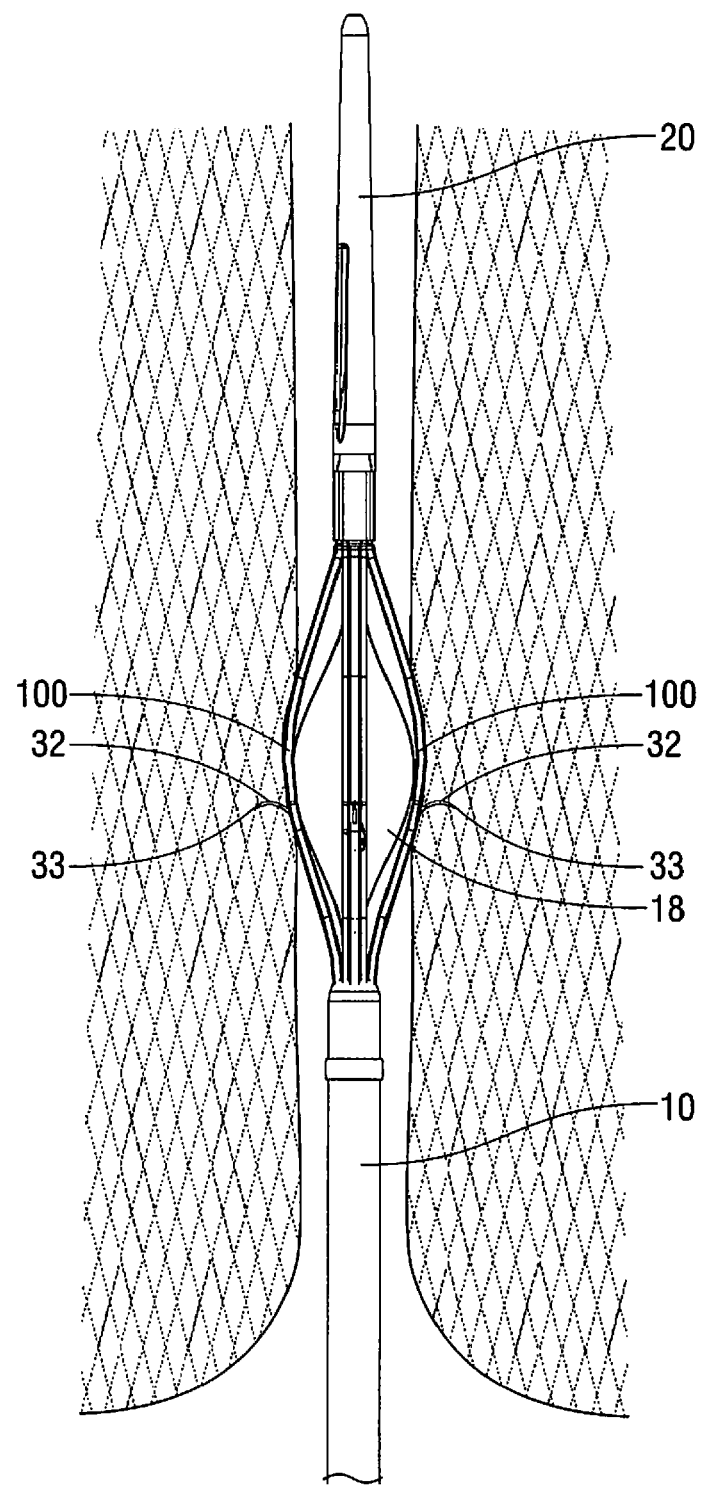

The electrodes 32 have sufficient distal sharpness and strength, when extended, to penetrate a desired depth into the smooth muscle of the lower esophageal sphincter 18 or the cardia of the stomach (see FIG. 38). The desired depth can range from about 3 mm to about 10 mm, and more preferably between about 5 mm to about 8 mm, although other depth ranges are also contemplated.

The electrodes 32 are formed of material that conducts radio frequency energy, such as by way of example nickel titanium, stainless steel, e.g., 304 stainless steel, or a combination of nickel titanium and stainless steel.

An electrical insulating material can be coated about the proximal end of each electrode so that when the distal end of the electrode penetrating the smooth muscle of the esophageal sphincter or cardia transmits radio frequency energy, the material insulates the mucosal surface of the esophagus or cardia from direct exposure to the radio frequency energy. Thermal damage to the mucosal surface is thereby avoided. The mucosal surface can also be actively cooled during application of radio frequency energy to further protect the mucosal surface from thermal damage.

The controller 9 can condition the electrodes 32 to operate in a monopolar mode. In this mode, each electrode 32 serves as a transmitter of energy, and an indifferent patch electrode (described later) serves as a common return for all electrodes 32. Alternatively, the controller 9 can condition the electrodes 32 to operate in a bipolar mode. In this mode, one of the electrodes comprises the transmitter and another electrode comprises the return for the transmitted energy. The bipolar electrode pairs can include electrodes on adjacent spines, or electrodes 32 spaced apart on different spines.

With reference to FIGS. 19-26, the needle electrodes are maintained in axial (longitudinal) and radial alignment. Each needle electrode 32 includes a location feature or structure in the form of two ribs or projections (bumps) 165, separated by grooves 166 for cooperation with grooves 97*a* formed between surfaces 97 of the needle holder 90. That is, the projections 165 are configured and dimensioned to fit within grooves 97*a*. Thus, during manufacture, the electrodes 32 are placed in alignment by a needle holder 90. A different number of projections and cooperating grooves is also contemplated, for the engagement structure. The bump/groove engagement can be a location feature which requires a clamp to maintain the position, or alternatively the location feature can interlock to frictionally engage. Also, alternatively, the projections could be provided on the needle holder and the grooves on the electrodes. Other engagement/location structure is also contemplated.

Figure 23A:
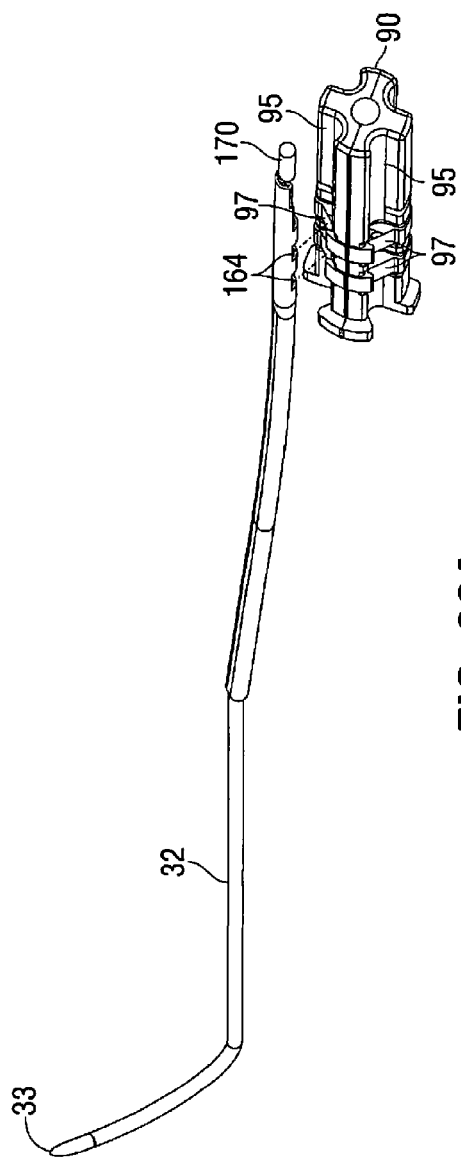
FIG. 23A is an isometric view showing the needle electrode of FIG. 19 being inserted into the needle holder of FIG. 22.
Figure 23B:
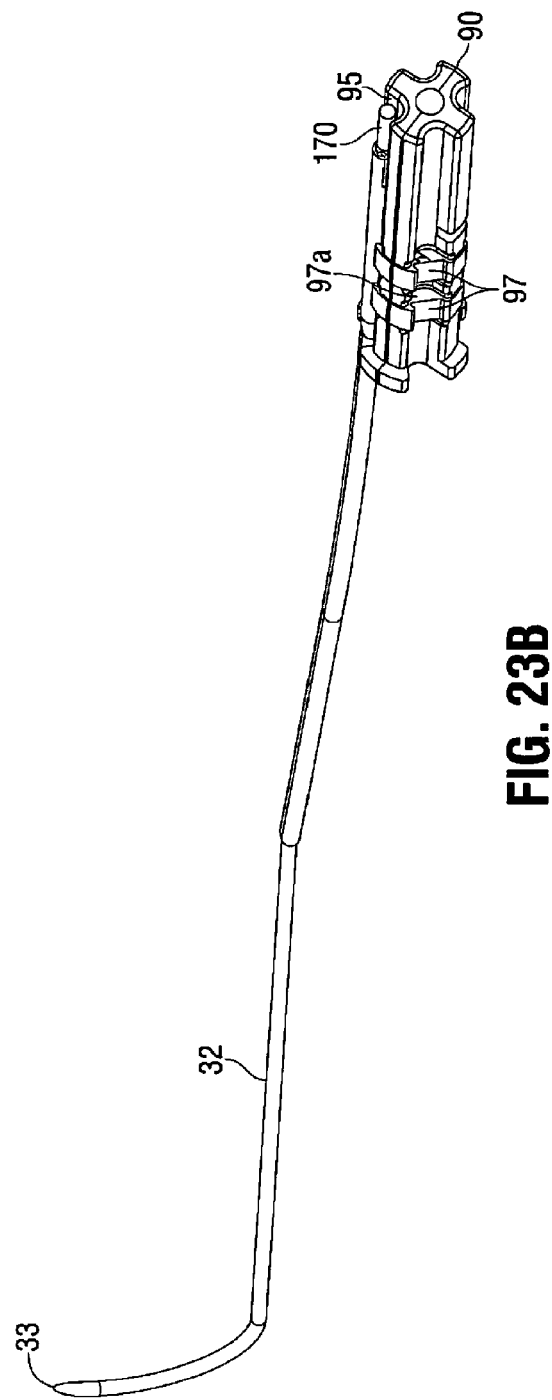
FIG. 23B is an isometric view similar to FIG. 23A showing the needle electrode positioned in the needle holder.
Figure 24:
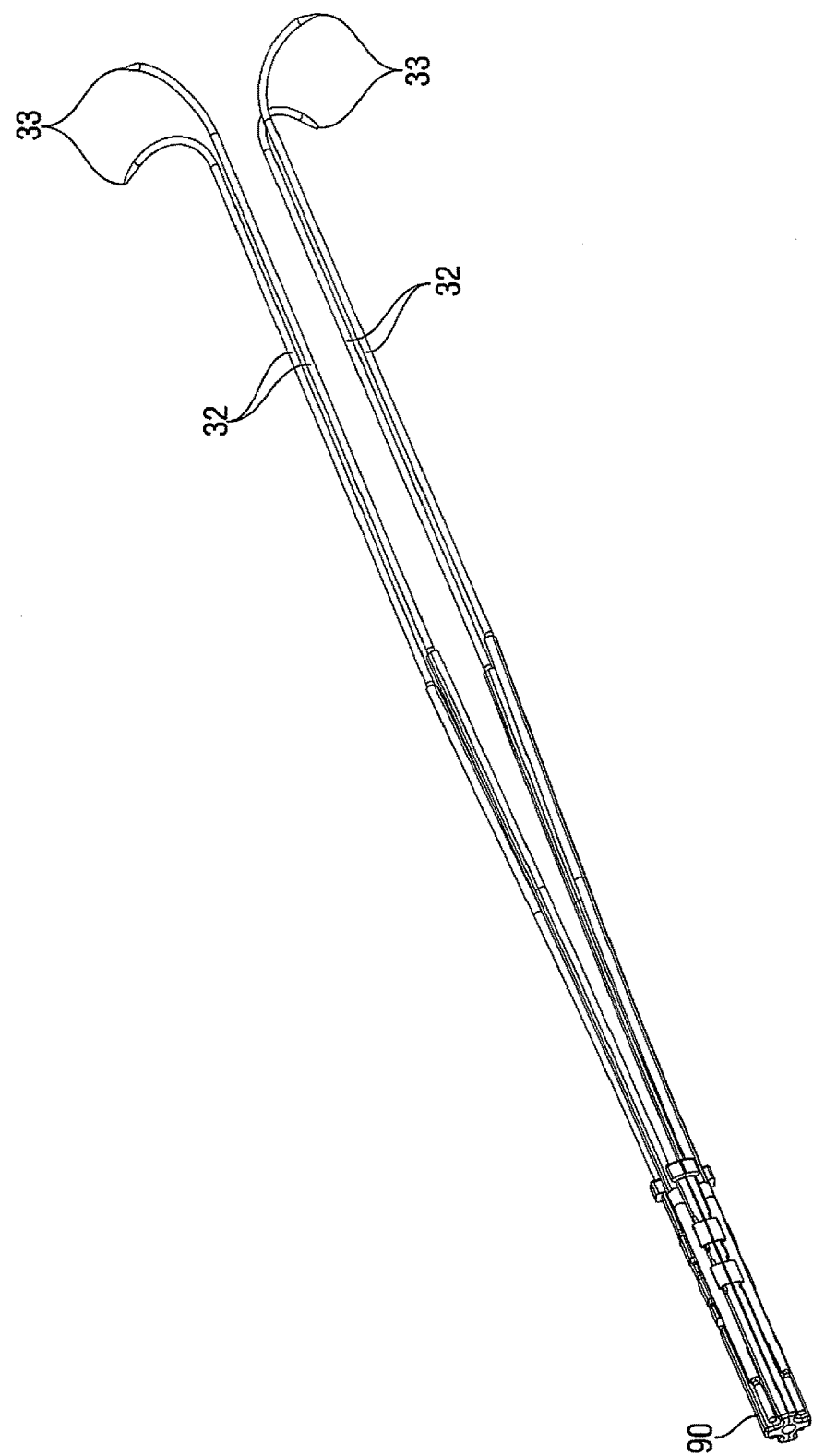
FIG. 24 is an isometric view illustrating the four needle electrodes positioned in the needle holder of FIG. 22.
Figure 25:
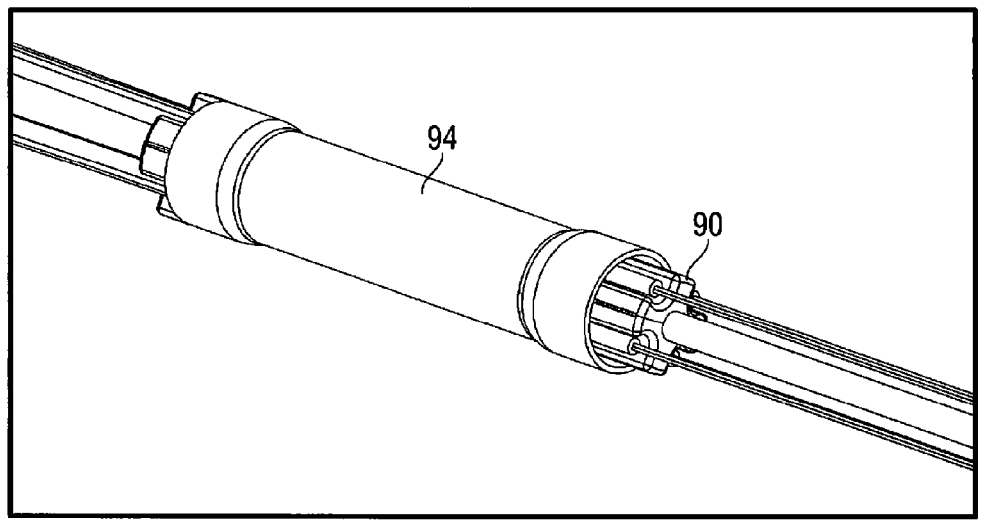
FIG. 25 is a close up view of the needle holder and sleeve.
Figure 26:
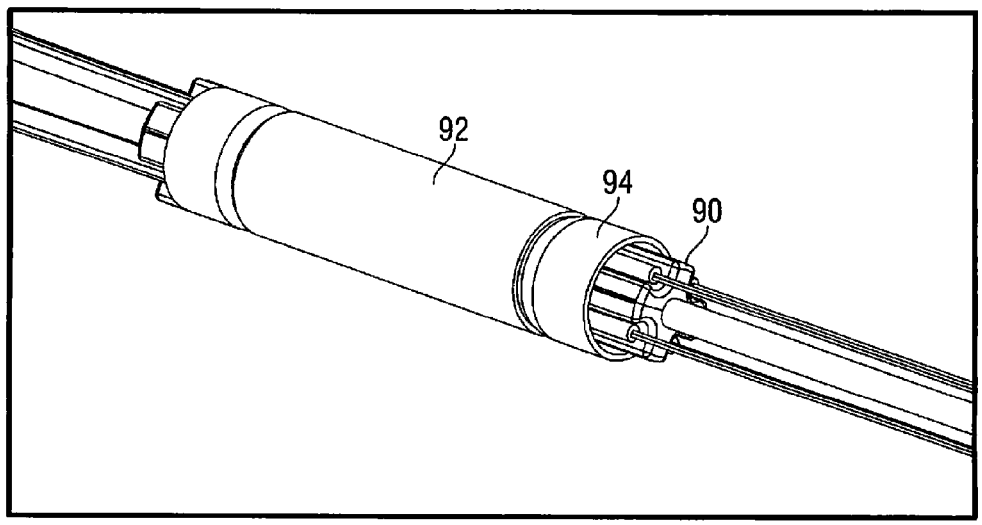
FIG. 26 is a view similar to FIG. 25 showing the tube clamp over the needle holder sleeve.
Figure 34A:
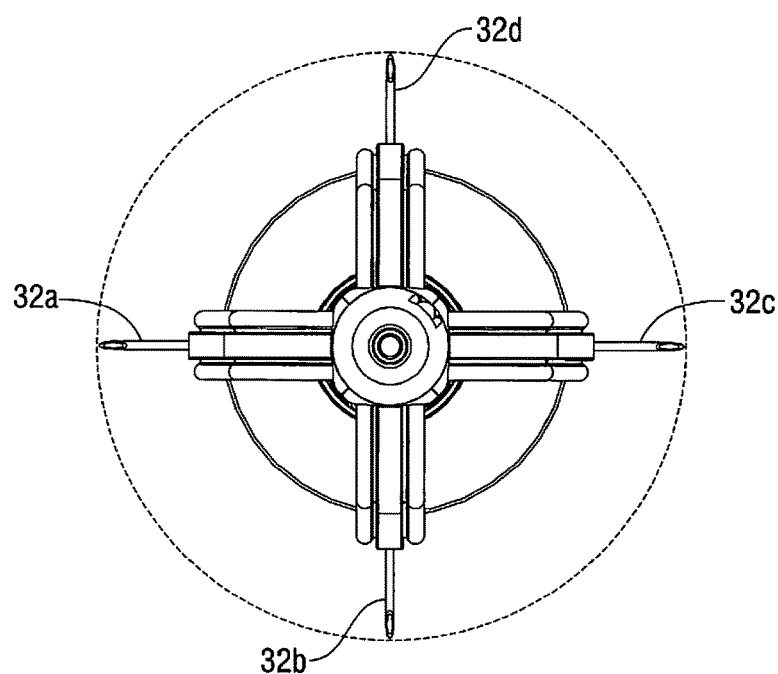
FIG. 34A is a front view of the device of FIG. 2A with the needle electrode in the deployed (advanced) position illustrating radial alignment of the needle tips.
Figure 34B:
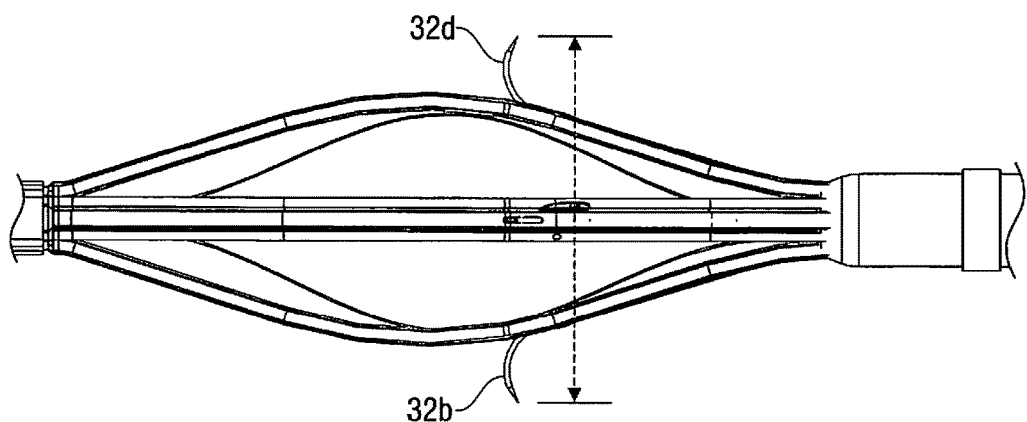
FIG. 34B is a side view of the basket and needle electrodes in the deployed position illustrating radial and longitudinal alignment of the needle electrode tips.

More specifically, FIG. 23A illustrates a needle electrode 32 just before engagement with the needle holder 90 and FIG. 23B illustrates engagement of the needle electrode with the projections/grooves of the needle holder 90. Each of the four needle electrodes 32 are interfit to the needle holder 90, separated at 90 degree intervals. Holder ring 94 is then placed over the needle holder 90 (FIG. 25) and clamping sleeve 92 (FIG. 25) is then placed over the ring 94 to provide a clamping force to hold the proximal ends of the needle electrodes 32 engaged with the needle holder 90, as shown in FIG. 26. The equidistant radial spacing and longitudinal alignment of the electrodes 32a-32d is illustrated in FIGS. 34A and 34B with the distal tips of the electrodes extending the same distance from the basket to terminate along the same plane. This is achieved by the aforedescribed location feature The advantage of the alignment of the electrodes 32 can be appreciated with reference to FIGS. 35A-35C showing misalignment. These Figures illustrate what can occur if the needle electrodes 32 are not properly aligned. In FIG. 35a, if the needle electrodes are not radially equidistantly spaced, then undertreatment and overtreatment areas will occur. For example, in FIG. 35a, a needle electrode 32a is shown out of axial alignment, i.e., more than 90 degrees apart from needle electrode 32b, and less than 90 degrees apart from needle electrode 32d. Optimally, when RF energy is applied to the tissue via the needle electrode tips, the treatment areas are spaced at a minimum of 5 millimeters apart, this occurs when the electrodes are properly aligned as in the present invention. After application of RF energy, and the device is rotated 45 degrees (or 30 degrees) to provide another application of RF energy, the treatment areas will be equidistantly spaced between the two treatment areas T1 and T2 provided the electrodes are properly aligned. However, if an electrode is out of axial alignment as is electrode 32a in FIG. 35A, space A between treatment area T3 and T4 is greater than 5 millimeters and space B between treatment areas T4 and T1 is less than 5 millimeters. Consequently, in the next application of RF energy after device rotation (FIG. 35B), treatment region T7 will be too close to treatment region T4, and can overlap region T4 which can overtreat the tissue and cause undesired tissue ablation. Conversely, treatment area T7 will be too far from treatment area T3 which will lead to undertreatment of tissue. Note new treatment region T5 is properly spaced from treatment regions T8 and T3.

The problem of misalignment and undertreatment/overtreatment is compounded since treatment is in three dimensions. That is, lesions are formed not only in an axial plane but in spaced longitudinal planes, and therefore proper spacing needs to be maintained not only in the axial lesion level, but between axial lesion levels. Therefore, when the device is moved axially to the next axial lesion level and the needle electrodes are deployed, the improper axial spacing will again cause tissue treatment areas too close or too far from other areas between axial planes.

A similar problem occurs if the needle electrodes are not longitudinally aligned i.e., the distal tips of the electrodes do not terminate the same distance from the spines 100. The locating feature of the present invention ensures that the needle electrodes distalmost end terminate at the same distal region. FIG. 35C illustrates what can occur if the needle electrodes are not longitudinally aligned in assembly and are deployed during use. As shown, improperly aligned electrode 32f terminates more proximally than electrode 32e since its initial position is improperly rearward of electrode 32f. When the electrodes are deployed, electrode 32f does not penetrate sufficiently into tissue so that when RF energy is applied, it will not treat the muscle layer but rather treat the mucosal layer. Conversely, if one of the needle electrodes is misaligned and is deployed too far, it can extend past the desired treatment area. When the device is moved to the next lesion level, the problem is compounded as the desired spacing between the treatment areas will not be maintained and RF energy in some regions will be applied too close to the previously treated area causing overheating and unwanted ablation and other regions will be applied too far from the previously treated region causing undertreatment.

As noted above, the basket arms 100 include the location feature to engage the feature on the basket holder 84. If the basket arms are not properly radially spaced e.g., not spaced equidistantly, then when the needle electrodes 32 are advanced through the apertures in the arms 100, they will not be equidistantly spaced, resulting in the undertreatment/ overtreatment of tissue discussed above. That is, if one of the arms 100 for example is improperly skewed so it is spaced more than 90 degrees from an adjacent arm, and closer than 90 degrees from the other adjacent arm, when the needle electrodes 32 are advanced from these arms, the tips would likewise be skewed and not spaced 90 degrees apart, resulting in the aforementioned problems of not maintaining the desired spacing.

Turning now to more details of the spacer 40, spacer 40 has a proximal end 40a connected to fastener 52 (FIG. 3) as discussed above. The distal end 40b (FIG. 4) connects to fastener 55, and can be flared as shown, and is retained within outer tube 22 by distal clamp 70. With reference to FIGS. 8A and 9-15, spacer 40 has a central circular rib 142 dimensioned to slidingly receive needle pusher 42. Emanating from the circular rib 142 are four transverse ribs 120, 122, 124 and 126 which subdivide the spacer 40 into four longitudinally extending quadrants 130, 132, 134, and 136. Thus, quadrant 130 is formed between ribs 120, 122, quadrant 132 is formed between ribs 122 and 124, quadrant 134 is formed between ribs 124 and 126 and quadrant 136 is formed between ribs 126 and 120. A pair of wires 50 are received in each of the quadrants, best shown in FIGS. 8 and 9, forming thermocouples for measuring tissue temperature of the tissue adjacent the needle electrodes 32. The spacer 40 is preferably in the form of a plastic tube formed by an extrusion. The spacer 40 also functions to maintain centering of the needle advancer during flexing of the catheter. That is, the slider/actuator 24 movement correlates one to one with movement of the needle advancer 42 and thus the needle electrodes 32. If not retained in the channel in the center then the needle electrodes 32 would be at a greater distance if the catheter tube 22 was bent in one direction and be at a shorter distance if the catheter 22 was bent in a different direction. This shorter distance can result in insufficient penetration resulting in undertreatment while on the other hand, movement a longer distance can result in over penetration. That is, this varied depth penetration can cause undertreatment or overtreatment which can lead to ablation of the tissue, as described in detail herein in conjunction with non-alignment of the electrodes and/or basket arms.

The outer wall 138 of spacer 140 is formed with slits to access each quadrant or area 130, 132, 136, and 138. More specifically, slit 140a enables access to area 130, slit 140b enable access to area 142, slit 140c enables access to area 134 and slit 140c enables access to area 136. The slit is separable during manufacture so the wires 50, irrigation tube 44 and aspiration tube 46 can be placed in the areas during manufacture. This facilitates manufacture, as the flap formed by the slit can be progressively opened and the wires and tube placed inside the area 130-136, with the flap self closing to retain the components within the spacer.

The spacer can in some embodiments be formed of a material more rigid than the outer tube. This enables a more flexible outer tube to be utilized as the spacer rather than the outer tube is utilized to provide a sufficiently rigid structure to retain the needle advancer.

Placement of all the wires and tubes are illustrated in FIG. 8A, with the thermocouple wires 50 placed in each of the quadrants 132-138. Irrigation tube 44 is within quadrant 134, balloon inflation tube 48 is within quadrant 138 and aspiration tube 46 is within quadrant 136.

Figure 8B:
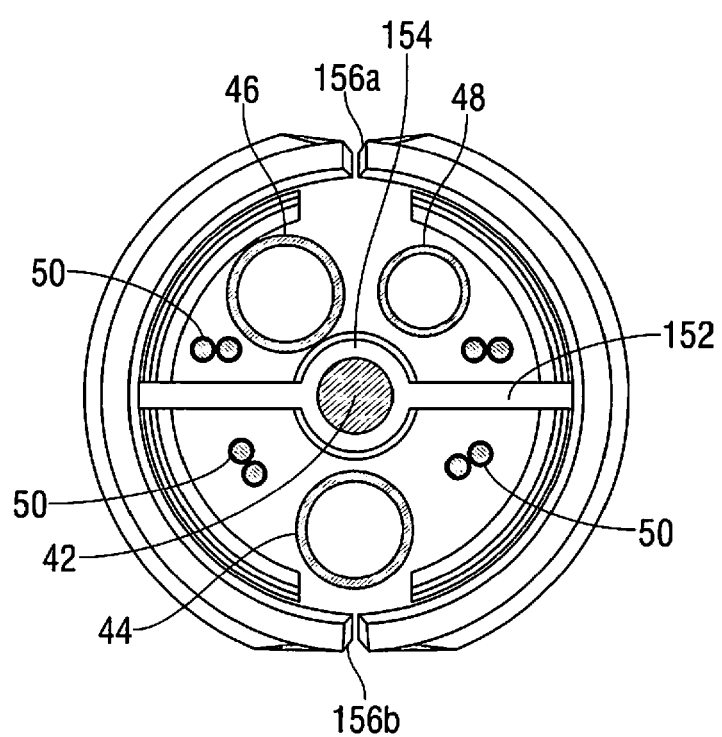
FIG. 8B is a front view of an alternate embodiment of the spacer.
Figure 13:
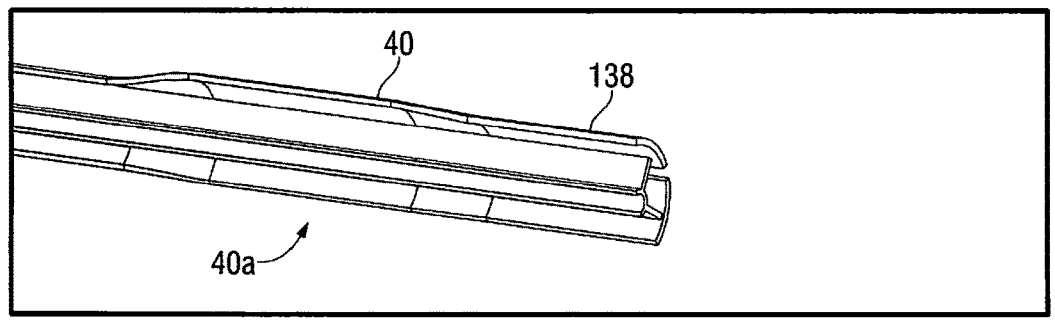
FIG. 13 is an enlarged isometric cross-sectional view of a distal portion of the spacer of FIG. 7.
Figure 14:
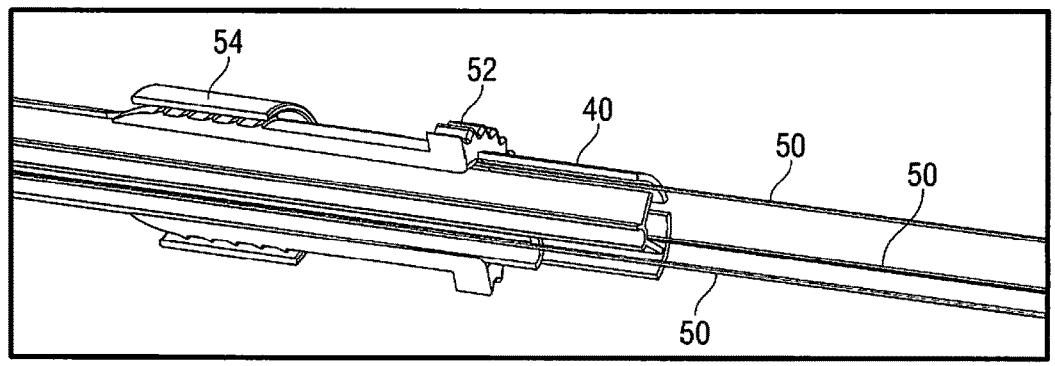
FIG. 14 is a view similar to FIG. 13 showing the holder and clamp.
Figure 15:
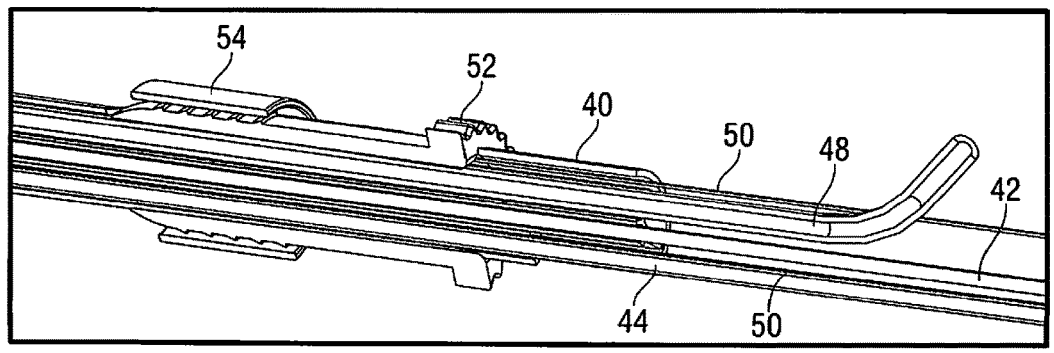
FIG. 15 is a view similar to FIG. 13 showing the holder, clamp and irrigation tube.

In the alternate embodiment of FIG. 8B, instead of four separate quadrants, a rib 152 extending from the outer wall transitions into circular rib 154 to retain the needle pusher 42 in a centered position within the spacer 40. Instead of four separate quadrants, some wires 50, aspiration tube 46, and balloon inflation tube 48 are placed in one quadrant and irrigation tube 44 and other wires 50 are placed in a second quadrant of the spacer 40. A slit 156a and 156b, similar to slits 140a and 140b of FIG. 8A, are provided to form a flap to enable access to the interior of the spacer in the same manner as described above. It should also be appreciated that a different number of ribs 152 can be provided to provide a different number of quadrants. For example, three ribs 152 can be provided to create three quadrants.

In the alternate embodiment of FIG. 12, instead of a single spacer, spacer 240 includes three separate spacers 240a, 240b and 240c with central lumens axially aligned. Alternatively, only two or more than three axially aligned spacers can be provided.

As noted above, the external fluid delivery apparatus 6 is coupled via tubing 6a (see FIG. 1) to connector 28 (see FIG. 4) to supply cooling liquid to the targeted tissue, e.g., through holes in the spines. The external aspirating apparatus 8 is coupled via tubing 8a (see FIG. 1) to connector or aspiration port 26 (see FIG. 3) to convey liquid from the targeted tissue site, e.g., through one of the tubes or lumens in the spines 100. The controller 9 can govern the delivery of processing fluid and, if desired, the removal of aspirated material.

Figure 36:
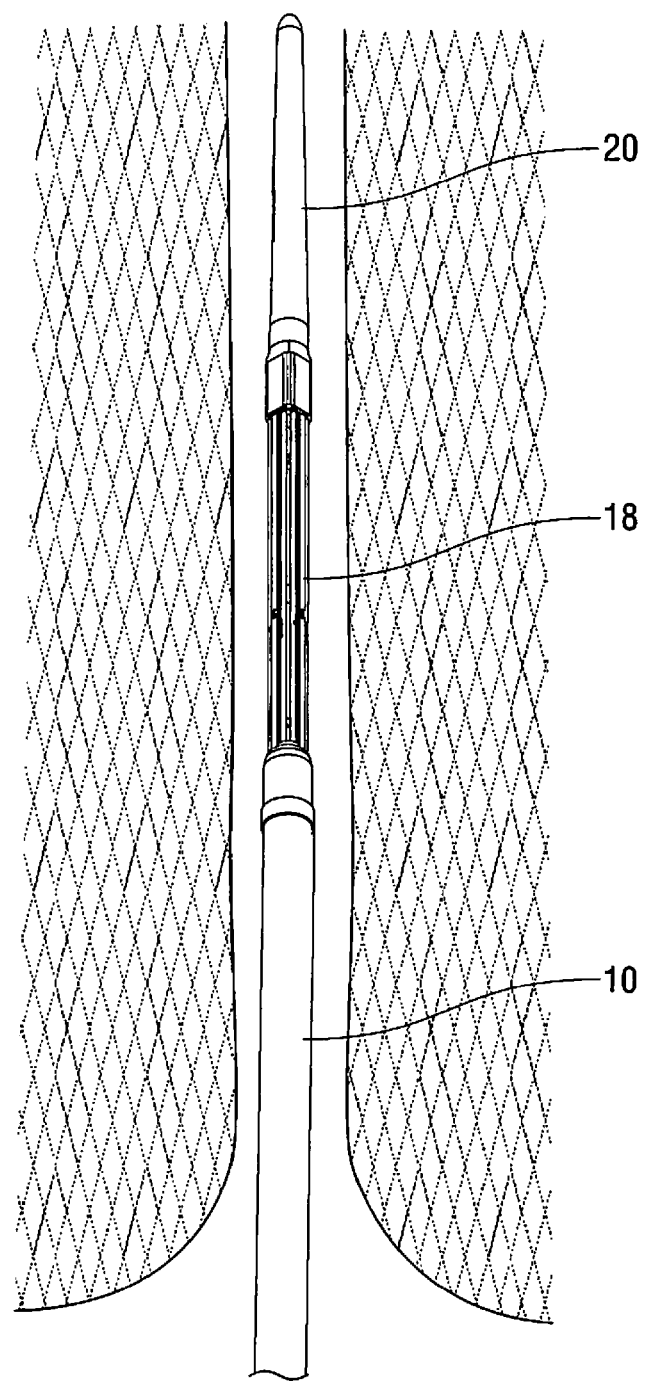
Figure 37:
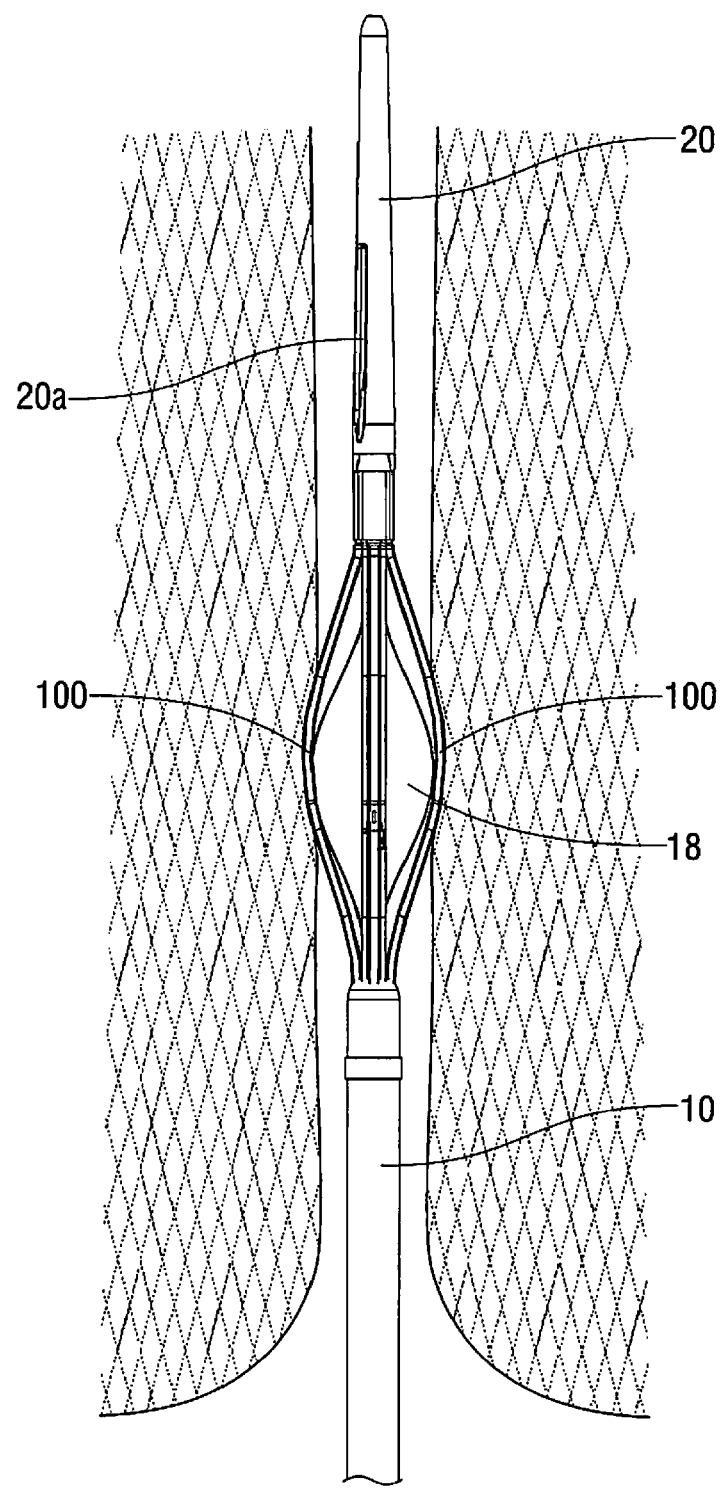
Figure 39:
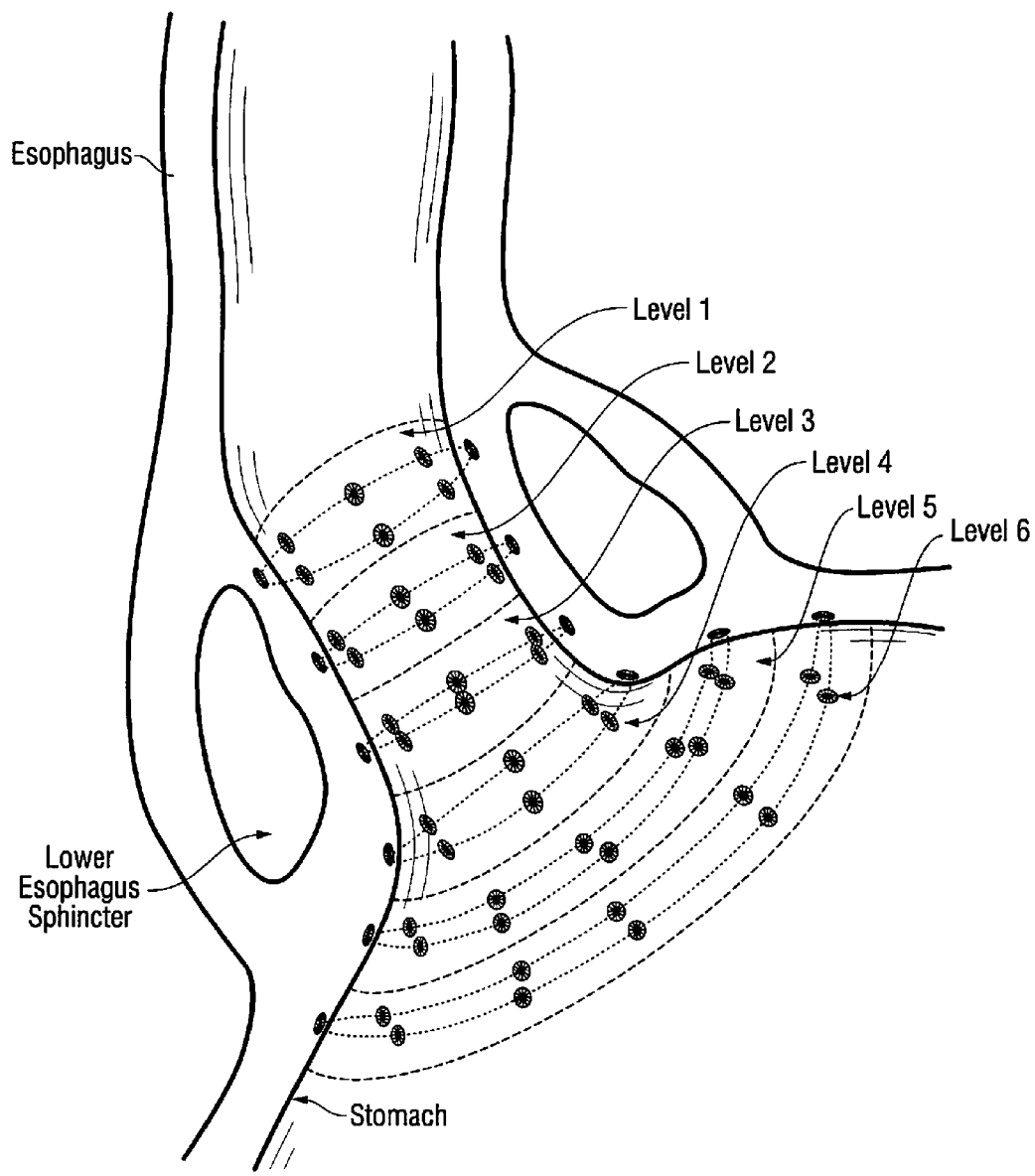
FIG. 39 illustrates the desired formation of lesions utilizing the aligned needle and basket assembly features of the present invention.

In use, the device 10 is manipulated to create a preferred pattern of multiple lesions comprising circumferential rings of lesions at several axially spaced-apart levels (about 5 mm apart), each level comprising from 8 to 12 lesions. A representative embodiment of the lesion pattern is shown in FIG. 39. The rings are preferably formed in the esophagus in regions above the stomach, at or near the lower esophageal sphincter, and/or in the cardia of the stomach. The rings in the cardia are concentrically spaced about the opening funnel of the cardia. At or near the lower esophageal sphincter, the rings are axially spaced along the esophagus. As shown, the device is inserted in the collapsed position of FIG. 36, expanded to the position of FIG. 37 by inflation of the balloon to dilate the sphincter and then the needle electrodes 32 are advanced into tissue as shown in FIG. 38 for application of energy.

Multiple lesion patterns can be created by successive extension and retraction of the electrodes 32, accompanied by rotation and/or axial movement of the catheter tube to reposition the basket assembly 18. The physician can create a given ring pattern by expanding the balloon structure 80 and extending the electrodes 32 at the targeted treatment site, to form a first set of four lesions. The physician can then withdraw the electrodes 32, collapse the balloon structure 80, and rotate the catheter tube 22 by a desired amount, e.g., 30-degrees or 45-degrees, depending upon the number of total lesions desired within 360-degrees. The physician can then again expand the structure 18 and again extend the electrodes 32, to achieve a second set of four lesions. The physician repeats this sequence until a desired number of lesions within the 360-degree extent of the ring is formed. Additional lesions can be created at different levels by advancing the operative element axially, gauging the ring separation by external markings on the catheter tube.

As shown in FIG. 39, a desirable pattern comprises an axially spaced pattern of six circumferential lesions numbered Level 1 to Level 6 in an inferior direction, with some layers in the cardia of the stomach, and others in the esophagus above the stomach at or near the lower esophageal sphincter. In the embodiment shown, in the Levels 1, 2, 3, and 4, there are eight lesions circumferentially spaced 45-degrees apart (i.e., a first application of energy, followed by a 45-degree rotation of the basket 56, followed by a second application of energy). In the Levels 5 and 6, there are twelve lesions circumferentially spaced 30-degrees apart (i.e., a first application of energy, followed by a 30-degree rotation of the basket 56, followed by a second application of energy, followed by a 30-degree rotation of the basket assembly 18, followed by a third application of energy). In Level 5, the balloon 80 is only partially expanded, whereas in Level 6, the balloon 80 is more fully expanded, to provide lesion patterns that increase in circumference according to the funnel-shaped space available in the funnel of the cardia.

Note that to secure against overinflation of the balloon, especially in tissue Levels 1-4 where the device is positioned in the esophagus, a pressure relief valve is attached to the air syringe, upstream of the balloon inflation port of the device, to allow air to escape if pressure levels are exceeded. That is, in Levels 1-4, the air syringe is filled with air, and the balloon is inflated to a target pressure so there is enough contact to slightly tension the tissue but not enough to stretch the tissue, with the pressure relief ensuring the pressure is not exceeded. Preferably, the balloon would be inflated to no more than about 2.5 psi. In the stomach, at Levels 5 and 6, there is more room for the balloon inflation, so the balloon can be further inflated and the pressure relief valve can be removed. The balloon is preferably inflated by volume to about 25 ml for treatment at Level 5, and after treatment at Level 5, deflated at Level 6 to about 22 ml. Note at Levels 5 and/or 6, the inflated balloon can also be used as an anchor. In an alternate embodiment, after treatment of Level 4 the balloon is deflated and the instrument is advanced, then retracted, wherein Level 6 is treated, then the instrument is pulled further proximally to subsequently treat Level 5. Stated another way, Level 5 can be considered in order of energy application so that it is distal of Level 6 and therefore being more distal, treated before Level 6. Note the balloon would still be inflated to about 25 ml in the more distal level and to about 22 ml in this embodiment. The balloon can also serve as an anchor.

In an alternate embodiment of the device 10, one or more digital cameras can be mounted along the catheter tube, e.g., with the camera lens directed to the basket assembly 18, to provide visualization of the site. In another alternate embodiment, the catheter tube can be designed to fit within a lumen of an endoscope, relying on the endoscope for visualization of the site.

A. Set-Up

In use, the GUI displays an appropriate start-up logo and title image (not shown), while the controller 52 performs a self-test. An array of SETUP prompts 502 leads the operator in a step-wise fashion through the tasks required to enable use of the generator and device. The GUI is described in detail in U.S. Patent Publication No. 2011/0112529, the entire contents of which are incorporated herein by reference and therefore for brevity is not repeated herein.

The physician can couple the source of cooling liquid to the appropriate port on the handle of the device 10 and load the tubing leading from the source of cooling liquid (e.g., a bag containing sterile water) into the pump. The physician can also couple the aspiration source 8 to the appropriate port on the handle of the treatment device 10. In the SET-UP prompt array, a graphic field of the GUI displays one or more icons and/or alpha-numeric indicia that prompt the operator to connect the return patch electrode, connect the foot pedal or switch, connect the selected treatment device 10 and to prime the irrigation pump.

Note in some embodiments, the user controls the pump speed to increase fluid flow if the temperature is rising. In alternate embodiments, the system is designed with an automatic cooling feature, thus enabling quicker application of cooling fluid to address rising tissue temperatures to faster cool the tissue surface which in turn cools the underlying tissue which helps to maintain the tissue temperature below the "tissue ablation threshold."

More specifically, at certain tissue temperatures, the speed of the pump is changed automatically to reduce the temperature. That is, if the tissue surface temperature, e.g., at the mucosa layer as measured by the tissue temperature sensor, reaches a certain threshold (a "first value"), the pump speed will increase to pump more cooling fluid to the tissue. In some embodiments, for certain tissue temperature values, the system can enable the user to override the automatic pump to reduce the fluid flow. In other embodiments, a user override feature is not provided. In either case, the system is preferably designed so that if a second predetermined higher temperature value ("second value") is reached, the pump is automatically moved to its maximum pump speed, which preferably cannot be overridden by the user. When a third predetermined still higher tissue temperature value is reached (a "third cutoff value"), the electrode channel is disabled as discussed herein to shut off energy flow to that electrode. Consequently, before the third cut off value is reached, as the temperature is rising, the system provides for a quicker response to the rising temperature by automatically increasing fluid flow, rather than relying on the slower response time of the user to implement the pump speed change, thereby helping to keep temperature below the tissue ablation threshold temperature.

Exemplary tissue values are provided solely by way of example, it being understood that other tissue values can also be utilized to achieve quick application of cooling fluid and ensure the non-ablation, and non-burning, of tissue. For example, in the upper GI tract treatment device described herein (see FIG. 2A), the first value could be about 38 degrees, the second value could be about 40 degrees and the third value where the energy is shut down could be about 43 degrees. For a lower GI tract treatment device, (such as the device of FIG. 6 of U.S. Publication 2011/0112529), the first value could be about 45 degrees, the second value could be about 46 degrees and the third value where the energy is shut down could be about 54 degrees.

In some embodiments, the identification code for the device is part of a printed circuit board (PCB) positioned in the handle of the treatment device. The PCB processes the calculated parameters. The PCB in conjunction with thermocouples provides a temperature measurement mechanism. The PCB measures the voltage generated by the thermocouples, converts it from an analog to a digital value and stores it in the internal memory. Upon request by the generator, the PCB communicates the digital data to the generator. This step is performed during the 100 millisecond break between radiofrequency pulses discussed below. By placement of the temperature measurement mechanism in the treatment device, i.e., in the disposable handpiece, rather than in the housing 400, data collection is closer to the source which translates into less noise susceptibility and improved accuracy. That is, since processing of temperature values occurs closer to the tissue and electrode tip, measurements can be more accurate. More accurate readings translate into tighter power controls and better clinical results and it better ensures the tissue is not ablated during treatment as it is maintained below a tissue ablation threshold.

In a preferred embodiment, the PCB, which is asymmetrically positioned within the handle, is shielded to reduce interference which could otherwise disrupt communication between the disposable treatment device and the generator. Such interference (noise) could corrupt the data and unnecessarily result in system errors which can unnecessarily shut down energy flow to the electrode(s) during the procedure. In a preferred embodiment, the shield is a copper foil, although other ways to shield the PCB are also contemplated. In other words, the disruption of communication could adversely affect processing and evaluation of the data collected by the treatment device. By eliminating such disruptions, and thereby disabling fewer electrodes, improved consistency of treatment is achieved. Also, as can be appreciated, if too many electrodes are disabled in a procedure, the tissue may not be sufficiently thermally treated to achieve the desired clinical result.

In an alternate embodiment, the identification code is positioned in the handle of the treatment device 10, but the other hardware, e.g., the printed circuit board for temperature calculation, etc. is outside the handle. Thus, the temperature data collection is performed outside the disposable treatment device which reduces costs since it need not be disposed of with the disposable treatment device. Note these embodiments still have the advantage of data collection closer to the source than if in the housing 400.

Upon completion of the SET-UP operation, the controller 52 proceeds to condition the generator and ancillary equipment to proceed step-wise through a sequence of operational modes. The operational modes have been preprogrammed to achieve the treatment protocol and objective of the selected device 10.

In the GUI, there is a parameter icon designating cooling fluid flow rate/priming. The Flow Rate/Priming Icon shows the selected pump speed by the number of bars, one bar highlighting a low speed, two bars highlighting a medium speed, and three bars highlighting a high speed.

Each GUI includes an Electrode Icon comprising an idealized graphical image, which spatially models the particular multiple electrode geometry of the device that has been coupled to the controller 42. This is illustrated and described in detail in U.S. Patent Publication No. 2011/0112529.

In some embodiments, temperature of the needle tips is measured when the needles are deployed at the lesion level, but prior to application of RF energy. If the measured temperature exceeds an expected value, the temperature reading alerts the user that the needle position might need to be readjusted. If the temperature value is too high, this can mean that the electrode position is too close to the previous tissue level treated, and thereby the user can readjust the electrode position by increasing the spacing, thereby reducing the chances of overtreating the tissue which can cause undesired tissue ablation or burning of tissue. Consequently, continuous treatment of tissue can be achieved with reduced overlapping of treatment.

Also, the temperature of the electrode tip, the tissue temperature and the impedance, along with other safety parameters, such as adequate connections, are monitored during the procedure to ensure energy flow is correct. This includes proper flow through the cable, electrodes, ground pad, etc. The electrode needle is then disabled if a safety condition is suspected and indicated. Each needle can be controlled separately.

In use of the system, impedance is intermittently checked throughout the procedure. Impedance is measured by measuring the current at the channel of the electrode tip. The impedance monitoring provides an indication of how well the treatment device is connected and communicating with the tissue, which includes the needle penetration and the path with the return pad. If there is not good contact between the electrode and tissue, impedance is high and a patient can get burned. Therefore, if a patient moves, needle penetration could be affected. However, oftentimes a minor adjustment can be made which does not require shutting down energy flow. To avoid premature shutting down of the system a multiple error check is conducted by the system which is described in more detail below. This multiple error check reduces the incidence of needle disabling which in turn reduces the incidence of undertreatment.

Note the impedance is measured by applying a voltage, measuring the current and calculating the impedance. In a preferred embodiment, the RF energy is applied in 0.9 second intervals, with a 0.1 second break in between where an artificial pulse is sent for 0.1 second, in which impedance is measured. The temperature of the electrode tip and tissue temperature is also measured during this 0.1 second interval, for calculating such measurement. Preferably, the RF energy is repeatedly applied for 0.9 seconds, with 0.1 second "measurement intervals" for a time period of 60 seconds.

There is also a Lesion Level Icon in each display adjacent to the respective Electrode Icon. The Lesion Level Icon comprises an idealized graphical image, which spatially models the desired lesion levels and the number of lesions in each level, described in detail in Patent Publication 2011/0112529. As described in this publication, the Lesion Level Icons change in real time, to step-wise guide the physician through the procedure and to record the progress of the procedure from start to finish.

The GUI graphically changes the display of the Lesion Levels, depending upon the status of lesion formation within the respective levels.

The Lesion Level Icons include a series of segmented circles. The open segments remaining in the segmented circle prompt the physician to rotate the basket by 45-degrees, and actuate the electrodes for second time. After the pre-set period (tracked by the Timer Icon), more treatment indicia (the dots) appear in the remaining segments of the circle. This indicates that all the lesions prescribed for Lesion Level 1 have been formed, and to deflate the basket and move to the next treatment level. The Marker that is displayed directs the physician to Lesion Level 2, which is 5 mm below Lesion Level 1. The Balloon Icon can reappear to prompt the physician to deflate the balloon.

The physician is thereby prompted to deflate the basket, move to Lesion Level 2, and expand the basket. Upon sensing electrode impedance, indicating contact with tissue at Lesion Level 2, the GUI changes the graphical form of Lesion Level 1 back to an edgewise cylinder. The edgewise cylinder for Lesion Level 1 includes an indicator, e.g., checkmark, to indicate that Lesion Level 1 has been treated. The insertion of the treatment completed indicator is yet another graphical form the GUI displays to communicate status information to the physician.

With the device positioned at Lesion Level 2, the physician actuates the electrodes for a first pre-set period, then rotates the device 45-degrees, and actuates the electrodes for the second pre-set period. The Timer Icon reflects the application of radio frequency energy for the pre-set periods, and the treatment indicia (e.g., dots) are added to the segments of the graphical segmented circle, indicating the formation of the first four lesions and the next four lesions, as well as their spatial orientation.

The physician is thereby prompted to deflate the basket, move to Lesion Level 3, and expand the basket upon sensing electrode impedance, indicating contact with tissue at Lesion Level 3.

The physician proceeds to form eight lesions in Lesion Level 3 then moving on to Lesion Level 4. All the while, the GUI visually records and confirms progress. On Lesion Levels 5 and 6, twelve lesions are to be formed. In the Levels 5 and 6, there are twelve lesions circumferentially spaced 30-degrees apart (i.e., a first application of energy, followed by a 30-degree rotation of the basket 18, followed by a second application of energy, followed by a 30-degree rotation of the basket 18, followed by a third application of energy). In Level 5, the balloon structure is only partially expanded, whereas in Level 6, the balloon structure is more fully expanded, to provide lesion patterns that increase in circumference according to the funnel-shaped space available in the funnel of the cardia.

Thus, the GUI, by purposeful manipulation of different stylized graphical images, visually prompts the physician step wise to perform a process of forming a pattern of lesions comprising a plurality of axially spaced lesion levels, each lesion level comprising a plurality of circumferential spaced lesions. The GUI registers the formation of lesions as they are generated in real time, both within and between each circumferentially spaced level. The GUI therefore displays for the physician a visual record of the progress of the process from start to finish. The GUI assures that individual lesions desired within a given level are not skipped, or that a given level of lesions is not skipped.

In the GUI, each Lesion Level 1 to 6 is initially depicted by a first stylized graphical image comprising an edgewise cylinder with a number identification of its level. When the formation of lesions at a given level is indicated, the GUI changes the first stylized graphical image into a second stylized graphical image, different than the first image, comprising an axial view of the cylinder, presented as a segmented circle, with the numbers of segments corresponding to the number of lesions to be formed. There also appears juxtaposed with the next lesion level to be treated (still displayed as an edgewise cylinder), a marker along with a number indicating its distance from the present legion level. As the physician manipulates the device to form lesions on the indicated levels, the second graphical image further changes to a third graphical image, different than the first or second images, by adding indicia within the segmented circle to reflect the formation of lesions, to guide the physician to successively rotate and operate the device at the lesion level. Upon forming the desired lesion pattern on a given level, the UGUI again changes the third graphical image to a fourth graphical image, different than the first, second, and third graphical images, comprising an edgewise cylinder with a number identification of its level, and further an indicator (e.g. a check mark) that indicates all desired lesions have been formed at the respective level. A Marker is successively updated to direct the physician to the next Lesion Level. In this way, the GUI prompts the formation of eight lesions circumferentially spaced 45-degrees apart in the Levels 1, 2, 3, and 4, and the formation of twelve lesions circumferentially spaced 30-degrees apart at Lesion Levels 5 and 6. Thus, a total of 56 lesions can be formed in this procedure.

During the procedure utilizing the radiofrequency treatment device 10, certain error messages are graphically indicated on the GUI. Certain of these error messages relate to user errors which could be in the user's control, and therefore could potentially be correctable by the user. For example, if there is an error in the treatment device connection, the generator returns to the set up screen and the icon representing the treatment device displayed by the GUI begins flashing. Another example is if the error relates to the return pad, e.g., improper placement or contact of the pad, the generator likewise returns to the set up screen and the return pad icon displayed by the GUI begins flashing. Another example is if the needles are not treated or positioned properly. With these errors indicated, the user can attempt to make the proper adjustments, e.g., check the connection of the treatment device, adjust the position of the return pad, etc. By easily identifying these correctible errors, the system will shut down fewer times thereby enabling the creation of more lesions. Stated another way, the instrument continuously measures temperature which is transmitted back to the generator. The generator expects the temperature to be in a certain range. If the temperature does not appear right, e.g., is outside an expected range, if the RF channel was immediately shut down, then it could result in premature/unnecessary termination of RF energy which could undertreat tissue. Therefore, the present invention provides steps to ensure a shut down result is truly necessary, thus advantageously limiting undertreatment of the tissue. Similarly, if calculated impedance from current measurement does not appear correct, i.e., is outside a desired range, e.g., 50-100 ohms for the instrument of FIG. 2A, 50-500 ohms for the instrument of FIG. 6 of U.S. Patent Publication 2011/0112529, and the system of the present invention ensures that a channel shut down is warranted before shut down, again avoiding premature/unnecessary termination of RF energy which can result in undertreatment of tissue.

The system, due to its faster processing speed which enables faster processing of data and faster adjustment of parameters, enables rechecking of detected errors to reduce the instances of prematurely shutting down energy flow to an electrode. As discussed above, premature termination of energy flow can result in insufficient application of thermal energy which in turn can result in undertreatment of tissue. In other words, the system advantageously is designed to reduce the number of events that would lead to energy cutoff to an electrode. More specifically, during the treatment cycles, oftentimes an error is detected which can be readily addressed by the user, such as by a small adjustment of the treatment device position if the error is caused for example by patient movement which affects the impedance reading, or even self-adjusts. If the system was designed to immediately shut down upon such error detection, then the electrode would be disabled and the lesion might not be created in that tissue region. Therefore, to reduce these occurrences, the system has been designed to recheck certain errors.

More specifically, for certain detected errors, the system does not permanently interrupt energy flow on the first error reading, but suspends energy flow until a second check of the system is performed. If on the second check the error is no longer detected, energy flow is resumed. However, if on the second check, e.g., re-measurement/calculation, an error still exists, the system runs yet a third check. If the error no longer exists, the energy flow resumes; if the error still exists, energy flow is cut off to that electrode at that treatment position. Consequently, only after the system runs a triple check is a final determination made to either transition back to energy flow or record the error and disable the electrode channel, i.e., shut down RF energy flow to that electrode. Thus, the error can be checked multiple times to ensure it actually requires interruption of energy flow, thus avoiding premature disabling of an electrode to thereby enhance tissue treatment by not skipping tissue levels, or regions (quadrants) within each tissue level which could otherwise have been treated. As a result, a more comprehensive and uniform tissue treatment is achieved.

This triple error checking feature exemplifies the speed of the processor which enables quicker processing of temperature calculations and quicker response to address rising temperatures so the tissue is not treated above the tissue ablation threshold. As noted above, this tissue ablation threshold can be exceeded if the energy is applied for too long a duration and/or too high a setting such that the tissue temperature rises or applied for too long a duration once the tissue temperature has reached the tissue ablation threshold before the flow of energy is terminated.

Also contributing to preventing overtreatment, as discussed above, is to ensure the spacing between the electrodes in manufacture is precise so during application of energy, the amount of overlapping in a circumferential orientation is reduced. Such accurate and consistent spacing can also prevent undertreatment such as if one of the circumferential array of electrodes is undesirably angled or curved too much toward another electrode, that would mean it is angled further away from an electrode on the opposite side, possibly creating a gap in the treatment in a circumferential orientation. The axial distance of the electrodes can also affect treatment. Therefore, maintaining the proper axial distance of the electrodes, preferably with the tips terminating at the same distal distance from the respective spine, and maintaining the proper radial distance of the tips, preferably evenly spaced along a circumference, will aid in maintaining the treatment between the lower threshold and maximum value threshold, i.e., between undertreatment and overtreatment.

The system, as noted above, also avoids ablating tissue due to careful and more accurate calibration of the tissue temperature measurement mechanism. This is basically achieved by precisely calibrating the PCB so it can read the voltage generated by the thermocouples more accurately, reducing the likelihood of heating tissue beyond the tissue ablation threshold. Thus, the PCB enables more accurate temperature measurements which in turn allows the system to disable or make the appropriate adjustment, e.g., increasing cooling fluid application, when the temperature limits are reached.

As discussed above, the centering of the needle pusher and attached electrodes, the alignment of the electrodes and the alignment of the basket arms maintain proper treatment zones to ensure the tissue is treated between the range of undertreatment and overtreatment.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method of treating gastrointestinal reflux disease comprising:
providing a treatment device having a plurality of electrodes, each of the plurality electrodes having an engagement feature to maintain distal tips of the plurality of electrodes in axial alignment when advanced from the treatment device, the treatment device further having a spacer with a central lumen to receive an electrode advancer to maintain centering of the electrode advancer within an outer tube of the treatment device during advancement;

applying non-ablative radiofrequency energy to the plurality of electrodes to thermally treat tissue below a tissue ablation threshold without causing tissue necrosis and create a plurality of tissue lesions along axially spaced tissue levels within the upper gastrointestinal tract;

monitoring tissue temperature throughout the procedure;

regulating power ensuring in response to the monitoring step that the tissue temperature does not exceed a predetermined value which would cause overheating of tissue which would cause tissue ablation and/or tissue necrosis; and rotating the device and subsequently applying non-ablative radiofrequency energy, the plurality of electrodes remaining in axial alignment to prevent overheating of tissue which would cause tissue necrosis.

2. The method for claim 1, wherein the distal tips of the plurality of electrodes are sharp to penetrate a muscle layer in a lower esophageal sphincter of a patient.

3. The method of claim 1, wherein the distal tips of the plurality of electrodes are maintained by the engagement feature in an equidistant radially spaced relationship, the equidistant relationship preventing overheating of tissue which would cause tissue necrosis.

4. The method of claim 1, wherein the plurality of electrodes are repeatedly advanced or retracted and maintained in equidistant radial spacing and longitudinal alignment when in an advanced position to prevent overheating of tissue which would cause tissue necrosis.

5. The method of claim 1, wherein the distal tips of the plurality of electrodes are longitudinally aligned to maintain control of depth of penetration of the plurality of electrodes.

6. The method of claim 1, wherein the treatment device has an expandable member having a plurality of arms, the plurality of arms have an alignment feature engageable with an arm holder to maintain alignment of the plurality of arms and the method includes a step of expanding the expandable member.

7. The method of claim 6, wherein the engagement features of the plurality of electrodes maintain an equidistant spacing of the distal tips of the plurality of electrodes.

8. The method of claim 1, wherein the spacer includes a plurality of separable slits forming openable and closable flaps for loading at least one wire therein.

9. The method of claim 1, wherein the spacer has a plurality of ribs forming separate enclosed regions.

10. The method of claim 9, wherein one of the separate enclosed regions is configured to receive an aspiration tube.

11. The method of claim 9, wherein one of the separate enclosed regions is configured to receive an irrigation tube.

12. The method of claim 1, further comprising a step of delivering fluid through the plurality of electrodes.

13. The method of claim 1, wherein the spacer has at least one slit separable to insert an irrigation tube and aspiration tube into the spacer.

14. The method of claim 1, wherein treatment areas for the plurality of electrodes are spaced at a minimum of 5 millimeters apart.

15. The method of claim 1, further comprising a step of executing on a display screen a first graphical interface guiding use of the treatment device, the display screen prompting a user in a step-wise fashion to perform a process using the treatment device to create the plurality of tissue lesions along axially spaced tissue levels, each axially spaced tissue level including a plurality of circumferential spaced lesions.

16. A method of treating tissue by applying non-ablative radiofrequency energy comprising the steps of:
   a. providing a device having an electrode advancer, a spacer to receive the electrode advancer and a plurality of electrodes movable between a retracted position and an advanced position, the plurality of electrodes each having a penetrating tip and a structure to maintain an equidistant radial spacing and to maintain longitudinal alignment of each of the penetrating tips of the plurality of electrodes;
   b. inserting the device into a sphincter of a patient;
   c. advancing the plurality of electrodes to penetrate sphincter tissue at a first location, the plurality of electrodes are configured to be longitudinally aligned in the advanced position and further being equidistantly radially spaced in the advanced position;
   d. applying non-ablative radio frequency energy to the plurality of electrodes to apply the non-ablative radiofrequency energy to tissue in a first area of the penetrating tips of the plurality of electrodes without causing tissue necrosis or tissue ablation with a minimum distance maintained between regions of tissue treated by the plurality of electrodes;
   e. retracting the plurality of electrodes within the device;
   f. rotating the device to a second position;
   g. advancing the plurality of electrodes from the device so that the penetrating tips penetrate sphincter tissue at a second location, the penetrating tips of the plurality of electrodes being longitudinally aligned and maintained in an equidistant radial spacing in the advanced position; and
   h. applying non-ablative radiofrequency energy to the plurality of electrodes to apply the non-ablative radiofrequency energy to tissue in a second area of the penetrating tips of the plurality of electrodes without causing tissue necrosis or tissue ablation, such equidistant radial spacing and longitudinal alignment maintain the minimum distance between regions of tissue treated to avoid overlapping of tissue treatment area which could cause ablation of tissue and tissue necrosis.

17. The method of claim 16, wherein the device includes an expandable basket having a plurality of arms, and further comprising a step of expanding the basket to dilate the sphincter, each of the plurality of arms having a structure to maintain a desired radial spacing of the plurality of arms in an expanded position of the basket, and the plurality of electrodes are movable within the plurality of arms.

18. The method of claim 16, wherein each penetrating tip of each of the plurality of electrodes has a defined treatment area and the structure by maintaining the radial spacing avoids undertreatment of tissue which could otherwise occur if each of the penetrating tips of each of the plurality of electrodes were not equidistantly radially spaced and the plurality of electrodes applied energy after rotation of the device to the second position.

19. The method of claim 16, wherein treatment areas of the plurality of electrodes are spaced at a minimum of 5 millimeters apart.

20. The method of claim 16, wherein the advancer for the plurality of electrodes is maintained centered during flexing of the device.

\* \* \* \* \*